(12) United States Patent
Lee et al.

(10) Patent No.: US 11,191,746 B2
(45) Date of Patent: Dec. 7, 2021

(54) COMPOSITION FOR INHIBITING A GROWTH OF CANCER STEM CELLS COMPRISING CICLESONIDE

(71) Applicant: JEJU NATIONAL UNIVERSITY INDUSTRY-ACADEMIC COOPERATION FOUNDATION, Eju-si (KR)

(72) Inventors: Dong-sun Lee, Jeju-si (KR); Hack Sun Choi, Jeju-si (KR)

(73) Assignee: JEJU NATIONAL UNIVERSITY INDUSTRY-ACADEMIC COOPERATION FOUNDATION, Jeju-si (KR)

( * ) Notice: Subject to any disclaimer, the term of this patent is extended or adjusted under 35 U.S.C. 154(b) by 0 days.

(21) Appl. No.: 16/341,132

(22) PCT Filed: Oct. 13, 2017

(86) PCT No.: PCT/KR2017/011284
§ 371 (c)(1),
(2) Date: Apr. 11, 2019

(87) PCT Pub. No.: WO2018/070819
PCT Pub. Date: Apr. 19, 2018

(65) Prior Publication Data
US 2020/0246307 A1 Aug. 6, 2020

(30) Foreign Application Priority Data
Oct. 14, 2016 (KR) .......................... 10-2016-0133358

(51) Int. Cl.
*A61K 31/357* (2006.01)
*A61P 35/04* (2006.01)

(52) U.S. Cl.
CPC ............ *A61K 31/357* (2013.01); *A61P 35/04* (2018.01)

(58) Field of Classification Search
CPC ..... A23L 33/10; A61K 31/357; A61K 31/573; A61K 31/58; A61P 35/04
See application file for complete search history.

(56) References Cited

U.S. PATENT DOCUMENTS

| | | | | |
|---|---|---|---|---|
| 2010/0135956 | A1* | 6/2010 | Gant | A61K 33/36 424/85.2 |
| 2012/0077786 | A1* | 3/2012 | Byron | A61K 31/573 514/167 |
| 2015/0010503 | A1* | 1/2015 | Szmulewitz | A61N 5/10 424/85.4 |

OTHER PUBLICATIONS

Podberezin (Cancer Stem Cells, Arch Pathol Lab Med, 137, Aug. 2013). (Year: 2013).*

* cited by examiner

*Primary Examiner* — Umamaheswari Ramachandran
(74) *Attorney, Agent, or Firm* — Lex IP Meister, PLLC

(57) ABSTRACT

The present invention relates to a composition for inhibiting the growth of cancer stem cells, which includes ciclesonide or a pharmaceutically acceptable salt thereof as an active ingredient, a pharmaceutical composition or food composition for inhibiting cancer metastasis, or treating or preventing cancer, which includes the composition, and the like. Ciclesonide of the present invention inhibits the growth of breast cancer cells and lung cancer cells, and inhibits the formation of breast cancer stem cells and lung cancer stem cells. In addition, it was confirmed that ciclesonide inhibited the expression of self-renewing genes such as Nanog, C-myc, Oct4, Sox2, Snail, and CD44, which are known to be characteristically expressed in breast cancer stem cells and lung cancer stem cells, inhibited the production of IL-6 and IL-8, which are known to be involved in the formation of mammospheres of breast cancer stem cells and the formation of tumorspheres of lung cancer stem cells, and inhibited the STAT3 signaling pathway. Accordingly, the compound inhibits the growth of cancer stem cells such as breast cancer stem cells, lung cancer stem cells, and the like and the growth of these cancers, and thus may be used for the treatment of cancer such as breast cancer, lung cancer, and the like.

7 Claims, 27 Drawing Sheets

Specification includes a Sequence Listing.

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: CD44 forward primer

<400> SEQUENCE: 1
agaaggtgtg ggcagaagaa                                               20

<210> SEQ ID NO 2
<211> LENGTH: 20
<212> TYPE: DNA
<213> ORGANISM: Artificial Sequence
<220> FEATURE:
<223> OTHER INFORMATION: CD44 reverse primer

<400> SEQUENCE: 2
aaatgcacca tttcctgaga                                               20

<210> SEQ ID NO 3
<211> LENGTH: 20
<212> TYPE: DNA
<213> ORGANISM: Artificial Sequence

```
<220> FEATURE:
<223> OTHER INFORMATION: NANOG forward primer

<400> SEQUENCE: 3
atgcctcaca cggagactgt                                              20

<210> SEQ ID NO 4
<211> LENGTH: 20
<212> TYPE: DNA
<213> ORGANISM: Artificial Sequence
<220> FEATURE:
<223> OTHER INFORMATION: NANOG reverse primer

<400> SEQUENCE: 4
aagtgggttg tttgcctttg                                              20

<210> SEQ ID NO 5
<211> LENGTH: 18
<212> TYPE: DNA
<213> ORGANISM: Artificial Sequence
<220> FEATURE:
<223> OTHER INFORMATION: OCT4 forward primer

<400> SEQUENCE: 5
agcaaaaccc ggaggagt                                                18

<210> SEQ ID NO 6
<211> LENGTH: 21
<212> TYPE: DNA
<213> ORGANISM: Artificial Sequence
<220> FEATURE:
<223> OTHER INFORMATION: OCT4 reverse primer

<400> SEQUENCE: 6
ccacatcggc ctgtgtatat c                                            21

<210> SEQ ID NO 7
<211> LENGTH: 23
<212> TYPE: DNA
<213> ORGANISM: Artificial Sequence
<220> FEATURE:
<223> OTHER INFORMATION: SOX2 forward primer

<400> SEQUENCE: 7
ttgctgcctc tttaagacta gga                                          23

<210> SEQ ID NO 8
<211> LENGTH: 20
<212> TYPE: DNA
<213> ORGANISM: Artificial Sequence
<220> FEATURE:
<223> OTHER INFORMATION: SOX2 reverse primer

<400> SEQUENCE: 8
ctggggctca aacttctctc                                              20

<210> SEQ ID NO 9
<211> LENGTH: 28
<212> TYPE: DNA
<213> ORGANISM: Artificial Sequence
<220> FEATURE:
<223> OTHER INFORMATION: Cmyc forward primer

<400> SEQUENCE: 9
aatgaaaagg ccccccaaggt agttatcc                                    28
```

```
<210> SEQ ID NO 10
<211> LENGTH: 20
<212> TYPE: DNA
<213> ORGANISM: Artificial Sequence
<220> FEATURE:
<223> OTHER INFORMATION: Cmyc reverse primer

<400> SEQUENCE: 10
gtcgtttccg caacaagtcc                                               20

<210> SEQ ID NO 11
<211> LENGTH: 20
<212> TYPE: DNA
<213> ORGANISM: Artificial Sequence
<220> FEATURE:
<223> OTHER INFORMATION: beta actin forward primer

<400> SEQUENCE: 11
tgttaccaac tgggacgaca                                               20

<210> SEQ ID NO 12
<211> LENGTH: 20
<212> TYPE: DNA
<213> ORGANISM: Artificial Sequence
<220> FEATURE:
<223> OTHER INFORMATION: beta actin reverse primer

<400> SEQUENCE: 12
ggggtgttga aggtctcaaa                                               20

<210> SEQ ID NO 13
<211> LENGTH: 22
<212> TYPE: DNA
<213> ORGANISM: Artificial Sequence
<220> FEATURE:
<223> OTHER INFORMATION: biotin upper strand of Stat3 probe

<400> SEQUENCE: 13
cttcatttcc cggaaatccc ta                                            22

<210> SEQ ID NO 14
<211> LENGTH: 22
<212> TYPE: DNA
<213> ORGANISM: Artificial Sequence
<220> FEATURE:
<223> OTHER INFORMATION: biotin lower strand of Stat3 probe

<400> SEQUENCE: 14
tagggatttc cgggaaatga ag                                            22

<210> SEQ ID NO 15
<211> LENGTH: 19
<212> TYPE: DNA
<213> ORGANISM: Artificial Sequence
<220> FEATURE:
<223> OTHER INFORMATION: Snail forward primer

<400> SEQUENCE: 15
accactatgc cgcgctctt                                                19

<210> SEQ ID NO 16
<211> LENGTH: 19
<212> TYPE: DNA
<213> ORGANISM: Artificial Sequence
<220> FEATURE:
<223> OTHER INFORMATION: Snail reverse primer
```

-continued

```
<400> SEQUENCE: 16
ggtcgtaggg ctgctggaa                                            19
```

COMPOSITION FOR INHIBITING A GROWTH OF CANCER STEM CELLS COMPRISING CICLESONIDE

TECHNICAL FIELD

The present invention relates to a composition for inhibiting the growth of cancer stem cells, which includes ciclesonide or a pharmaceutically acceptable salt thereof as an active ingredient, a pharmaceutical composition or food composition for inhibiting cancer metastasis, or treating or preventing cancer, which includes the composition, and the like.

BACKGROUND ART

As anticancer therapies are unable to effectively target a population of cells in a tumor and lead to tumor recurrence and metastasis, interest in cancer stem cells (CSCs) has been increasing. Many cytotoxic anticancer agents mostly target rapidly proliferating cells, and thus cancer stem cells, which slowly proliferate, are able to survive cytotoxic chemotherapy. Basal cell phenotype breast cancer is considered to have originated from the earliest mammary progenitor cells in a differentiation process, and is known to have poor prognosis and resistance to existing anticancer therapies, and this may be a good example showing that the failure of anticancer therapies is due to the failure of targeting treatment for CSCs.

Several therapies have been devised based on the cancer stem cell hypothesis, and thereamong, the most common method is a method using the self-renewal pathway of CSCs. In this treatment, it is important that only the self-renewal of cancer stem cells be targeted while maintaining the self-renewal of normal stem cells. For example, the Notch signal is activated by an enzyme called secretase, and when secretase inhibitors are used in Notch1-overexpressing breast cancer, a tumor-inhibiting effect may be obtained. It has recently been reported that targeting the Hedgehog signaling pathway also exhibits an anticancer effect, and according to the report, when a tumor xenograft animal was administered cyclopamine, which is a Hedgehog inhibitor, the size of tumors was dramatically reduced.

Meanwhile, breast cancer is a common cancer in women and is known to be a major cause of death in female cancer patients (al A, Bray F, Center M M, Ferlay J, Ward E and Forman D. Global cancer statistics. CA Cancer J Clin. 2011; 61(2):69-90). In early breast cancer, extensive mammograms and adjuvant therapies along with polychemotherapy and tamoxifen have reduced the mortality rate of breast cancer, but breast cancer is still known to be the most dangerous disease due to recurrence and metastasis. CSCs were first identified in myeloid leukemia and subsequently found in a variety of solid cancers, including breast cancer, brain cancer, colon cancer, ovarian cancer, pancreatic cancer, prostate cancer, and the like. CSCs are also referred to as tumor-initiating cells and cancer stem-like cells. It has also been shown that various types of cancer including breast cancer are derived from CSCs, which are a tumor subpopulation. This subpopulation is known to induce a change in tumor volume through self-renewal and differentiation. Wnt (wingless), Shh (Sonic hedgehog), Stat3, NF-κB, Wnt/β-catenin, TGF-β, and Notch signaling pathways are known to be critical for self-renewal of CSCs.

CSCs exhibit drug resistance and radiation resistance to chemotherapy and radiation therapy, and cause cancer recurrence and metastasis. Therefore, targeting treatment for CSCs is essential for cancer treatment. CSCs are known to express specific proteins including Oct4, C-myc, Nanog, and aldehyde dehydrogenase-1 (ALDH). ALDH is an enzyme that oxidizes genetic toxic aldehyde, and its enzymatic activity is widely used as a CSC marker of leukemia, head and neck cancers, bladder cancer, bone cancer, colon cancer, liver cancer, lung cancer, pancreatic cancer, prostate cancer, thyroid cancer, and cervical cancer. ALDH is known as a therapeutic target of CSCs. It is also known that ALDH has an excellent ability to form tumors in breast cancer groups expressing CD44+/CD24− in clinical samples (Al-Hajj M, Wicha M S, Benito-Hernandez A, Morrison S J and Clarke M F. Prospective identification of tumorigenic breast cancer cells. Proc Natl Acad Sci USA. 2003; 100(7):3983-3988).

Signal transducers and activators of transcription 3 (Stat3) are mainly activated in CSCs, and mammosphere formation is associated with the JAK1-STAT3 pathway. Secreted IL-6 activates the JAK1-STAT3 pathway and increases the expression of the Oct4 gene. The IL-6/JAK1/STAT3 signaling pathway is known to be important for conversion of NSCCs (Non-CSCs) to CSCs. Blocking of the STAT3 signaling pathway is known to inhibit the growth of CD44+/CD24− stem cell-like cells derived from breast cancer cells. Nuclear factor-κB (NF-κB) transcription factors are structurally (constantly) activated in tumor cells including colon cancer cells, breast cancer cells, and liver cancer cells, and regulated by IκB kinase (IKK) complexes. Pyrrolidine dithiocarbamate (PDTC), which is an NF-κB inhibitor, is known to inhibit breast cancer stem-like cells.

It is known that breast cancer stem cells can be identified by the expression of biomarkers such as $CD44^{high}/CD24^{low}$, ESA+ (epithelial specific antigen), and ALDH. Chemotherapy is known to increase the proportion of cancer cells expressing CD44+/CD24− and the formation of mammospheres. CSCs overexpress specific ABC transporters to protect CSCs from toxins. ABC pumps are used to isolate a side population (SP) and can be classified by ABCG2 transporter-specific Hoechst 33342 dyes. Breast CSCs produce reactive oxygen species (ROS) at a lower level than that of tumor cells, and thus breast cancer stem-like cells have radiation resistance. It is known that this is because ROSs are major mediators of ionizing radiation-induced apoptosis, and thus DNA damage of CSCs is less than that of non-stem cancer cells (Diehn M, Cho R W, Lobo N A, Kalisky T, Dorie M J, Kulp A N, Qian D, Lam J S, Ailles L E, Wong M, Joshua B, Kaplan M J, Wapnir I, Dirbas F M, Somlo G, Garberoglio C, et al. Association of reactive oxygen species levels and radioresistance in cancer stem cells. Nature. 2009; 458(7239):780-783).

The breast cancer cell line MCF-7 is known to have a partial colony of cells with stem cell-like capability to grow into elliptical cells without apoptosis even without adherence in vitro. Cells with stem cell-like properties are attached to each other under a substrate layer-free condition artificially made by floating culture, thereby forming spherical cell aggregates, so-called neurospheres. Human breast stem cells to which this concept is applied are called "mammospheres." Mammospheres contain progenitor cells in an amount that is 8 times greater than that in normal human breast cells and can be continuously sub-cultured, and after several stages of sub-culture, 100% of mammospheres grow into bi-potent precursor cells. Mammospheres can be differentiated into mammary gland epithelial cells, which are adult breast cells, ductal epithelial cells, and alveolar epithelial cells, and are observed to form a three-dimensional structure and a complicated functional breast structure in Matrigel. Mammospheres have a self-proliferative ability, which is one of the most characteristic features of stem cells, and thus several mammospheres or breast stem cells may be obtained in a large amount from a single mammosphere. It has also been confirmed that many expression genes are overlapped in mammospheres compared to hematopoietic stem cells, neural stem cells, embryonic stem cells, and the like, and thus mammospheres have been reported to be actual breast stem cells. A standard method of analyzing the self-renewal ability of these CSC is to analyze in vivo transplantation and in vitro mammosphere formation.

In addition, in various cancer cell lines including a lung cancer cell line as well as a breast cancer cell line, cells with stem cell-like properties are attached to each other to thereby form a spherical cell aggregate, which is called a tumorsphere. The tumorsphere refers to a tumorsphere developed by the proliferation of a single CSC or cancer precursor cell.

Meanwhile, lung cancer is a major cause of cancer-related death in the world, and as two major subtypes thereof, there are non-small cell lung cancer (NSCLC) and small cell lung cancer (SCLC). NSCLC accounts for 85% of lung cancer patients, and SCLC accounts for 15%. NSCLC is divided into three subtypes: adenocarcinoma, squamous cell cancer, and large cell cancer. Smoking is a major risk factor for lung cancer. Lung cancer can be treated by chemotherapy and radiation therapy, but has become resistant to the therapies. The 5-year survival rate of lung cancer is low, the 1-year survival rate of small cell lung cancer is 40%, and the 5-year survival rate of small cell lung cancer is 5% or less. However, the mechanism of resistance to radiation therapy and chemotherapy in lung cancer is not well known. CSCs have drug resistance and radiation resistance to chemotherapy and radiation therapy, which are used to eradicate bulk tumors, resulting in cancer recurrence and metastasis. Thus, targeting treatment for CSCs is essential for lung cancer treatment.

To date, research on CSCs has been greatly limited, and the role of CSCs in tumor formation or maintenance has not been found. To effectively perform targeting treatment for only CSCs without damaging normal stem cells, knowledge and understanding of molecular biological characteristics or regulatory pathways thereof, which are important for maintaining and regulating CSCs, are needed.

DISCLOSURE

Technical Problem

To date, there have been few studies on an anticancer agent or natural substance-derived extract that directly targets cancer stem cells. In the related art, as experiments for inhibiting direct target genes of cancer stem cells, studies on inhibition of cancer stem cells or inhibition of cancer stem cells by inhibiting an upstream signaling protein of cancer stem cells were conducted. However, these targeting experiments have had difficulties in many tumor patients due to oncogene mutation or protein mutation.

Technical Solution

In accordance with an aspect of the present invention, the above and other objects can be accomplished by the provision of a composition for inhibiting the growth of a cancer stem cell, which includes ciclesonide represented by Formula 1 or a pharmaceutically acceptable salt thereof as an active ingredient.

In accordance with another aspect of the present invention, there is provided a pharmaceutical composition for treating or preventing cancer, which includes the composition for inhibiting the growth of a cancer stem cell.

In accordance with another aspect of the present invention, there is provided a pharmaceutical composition for inhibiting cancer metastasis, which includes the composition for inhibiting the growth of a cancer stem cell.

In accordance with another aspect of the present invention, there is provided a food composition for alleviating or preventing cancer, which includes the composition for inhibiting the growth of a cancer stem cell.

In accordance with another aspect of the present invention, there is provided a food composition for alleviating or preventing cancer metastasis, which includes the composition for inhibiting the growth of a cancer stem cell.

In accordance with another aspect of the present invention, there is provided a method of inhibiting the growth of a cancer stem cell, which includes administering ciclesonide represented by Formula 1 or a pharmaceutically acceptable salt thereof to an individual.

In accordance with another aspect of the present invention, there is provided a method of inhibiting cancer metastasis, which includes administering ciclesonide represented by Formula 1 or a pharmaceutically acceptable salt thereof to an individual.

In accordance with another aspect of the present invention, there is provided a method of preventing or treating cancer, which includes administering ciclesonide represented by Formula 1 or a pharmaceutically acceptable salt thereof to an individual.

In accordance with another aspect of the present invention, there is provided a use of ciclesonide represented by Formula 1 or a pharmaceutically acceptable salt thereof for preparing a drug for inhibiting the growth of a cancer stem cell.

In accordance with another aspect of the present invention, there is provided a use of ciclesonide represented by Formula 1 or a pharmaceutically acceptable salt thereof for preparing a drug for inhibiting cancer metastasis.

In accordance with another aspect of the present invention, there is provided a use of ciclesonide represented by Formula 1 or a pharmaceutically acceptable salt thereof for preparing a drug for preventing or treating cancer.

Advantageous Effects

Ciclesonide of the present invention inhibited the growth of breast cancer cells and lung cancer cells, and inhibited the formation of breast cancer stem cells and lung cancer stem cells. In addition, it was confirmed that ciclesonide inhibited the expression of self-renewing genes such as Nanog, C-myc, Oct4, Sox2, Snail, and CD44, which are known to be characteristically expressed in breast cancer stem cells and lung cancer stem cells, inhibited the production of IL-6 and IL-8, which are known to be involved in the formation of mammospheres of breast cancer stem cells and the formation of tumorspheres of lung cancer stem cells, and inhibited the Stat3 signaling pathway. Accordingly, the compound inhibits the growth of cancer stem cells such as breast cancer stem cells, lung cancer stem cells, and the like and the growth of these cancers, and thus can be used for the treatment of cancer such as breast cancer, lung cancer, and the like.

DESCRIPTION OF DRAWINGS

FIG. 1 illustrates inhibition of various cancer characteristics by ciclesonide in breast cancer cell lines, wherein

FIG. 2 illustrates an effect of ciclesonide on tumor growth in a xenograft model, wherein 3,000,000 cells were injected into the breast fat pad of each immunodeficient NOD-SCID female nude mouse.

*$p<0.05$ compared to a control, representative images were captured at the end of 7 weeks of treatment, and the results were shown for a vehicle-treated control and ciclesonide-treated mice.

Figure 3A:
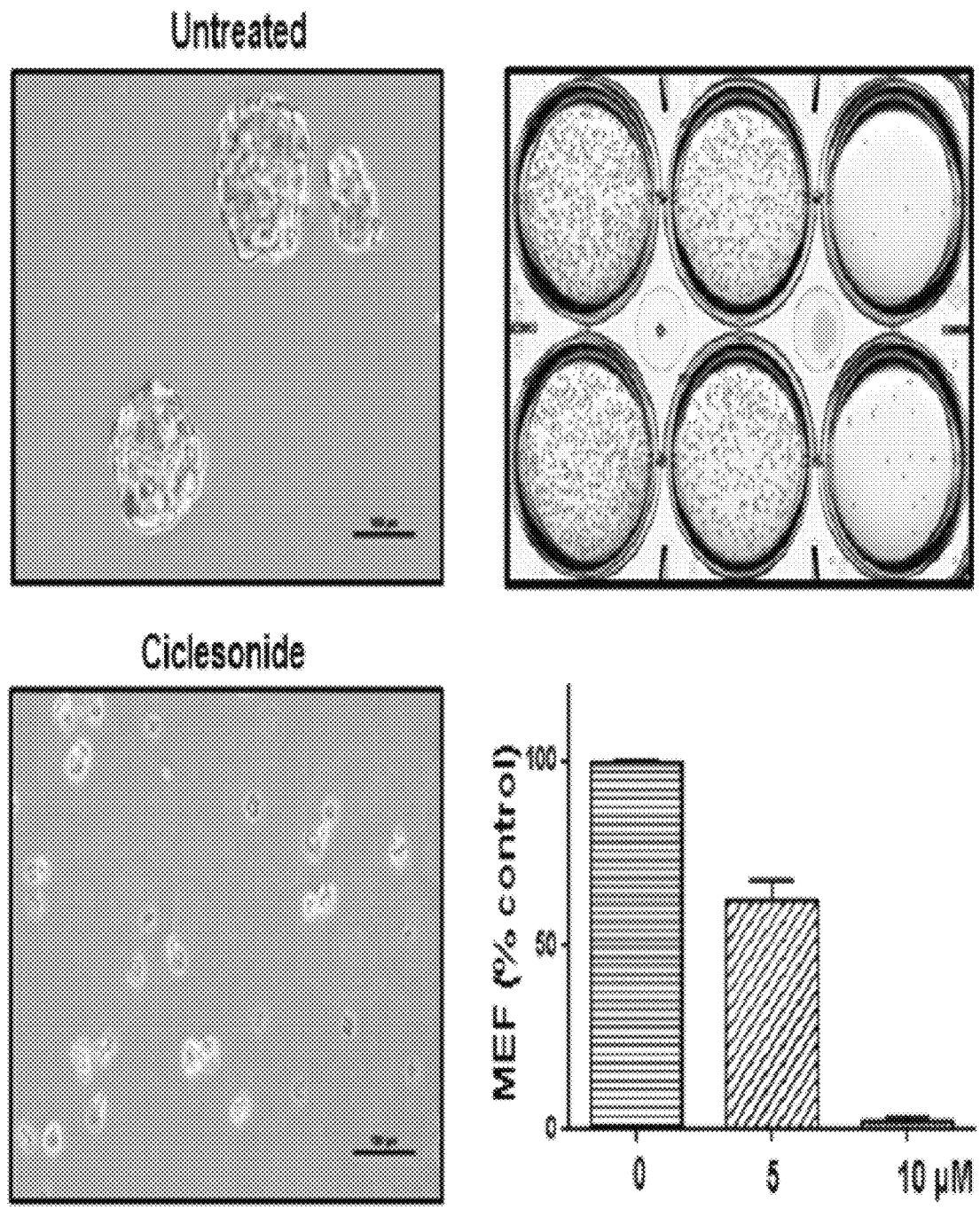
Figure 3B:
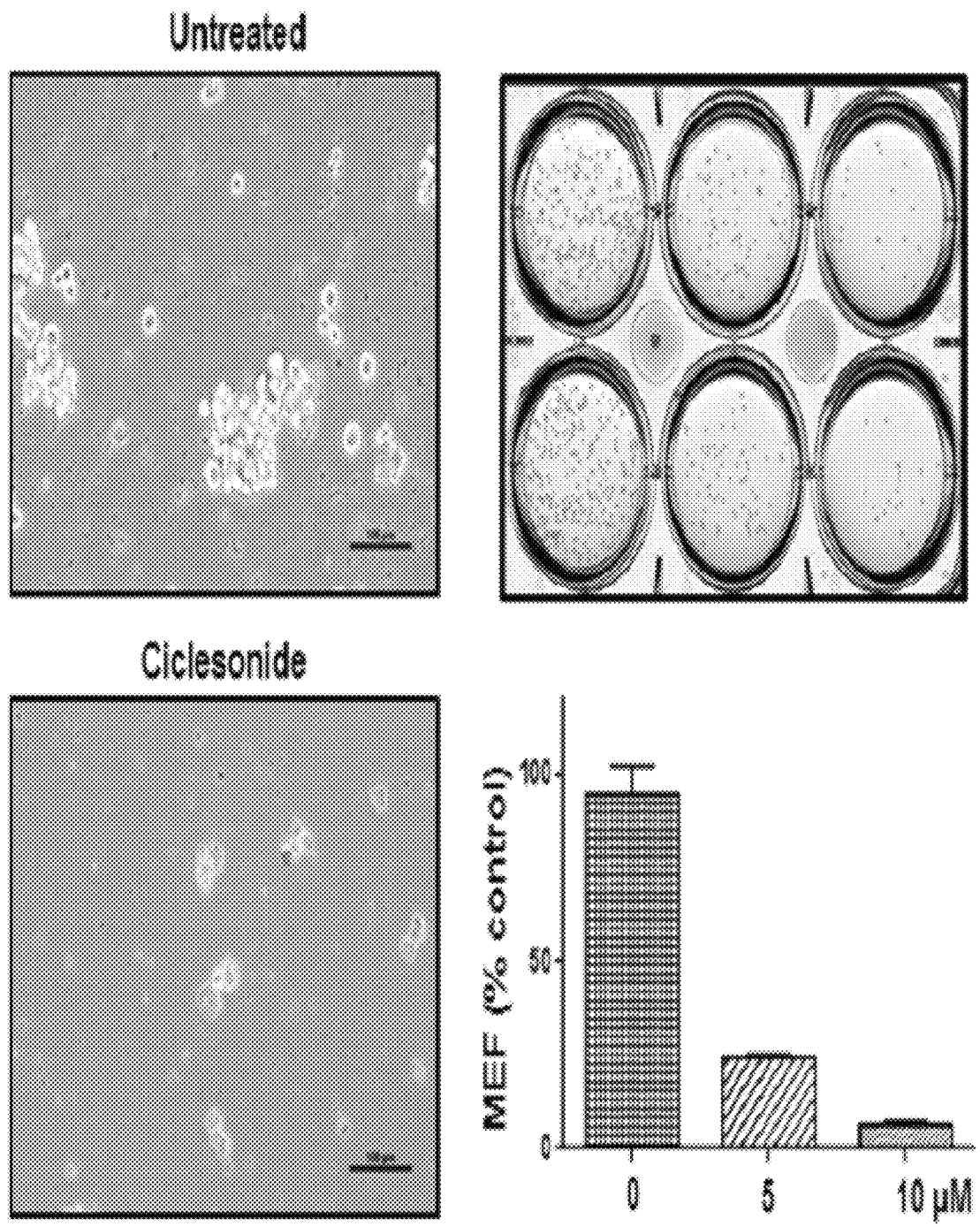
Figure 3C:
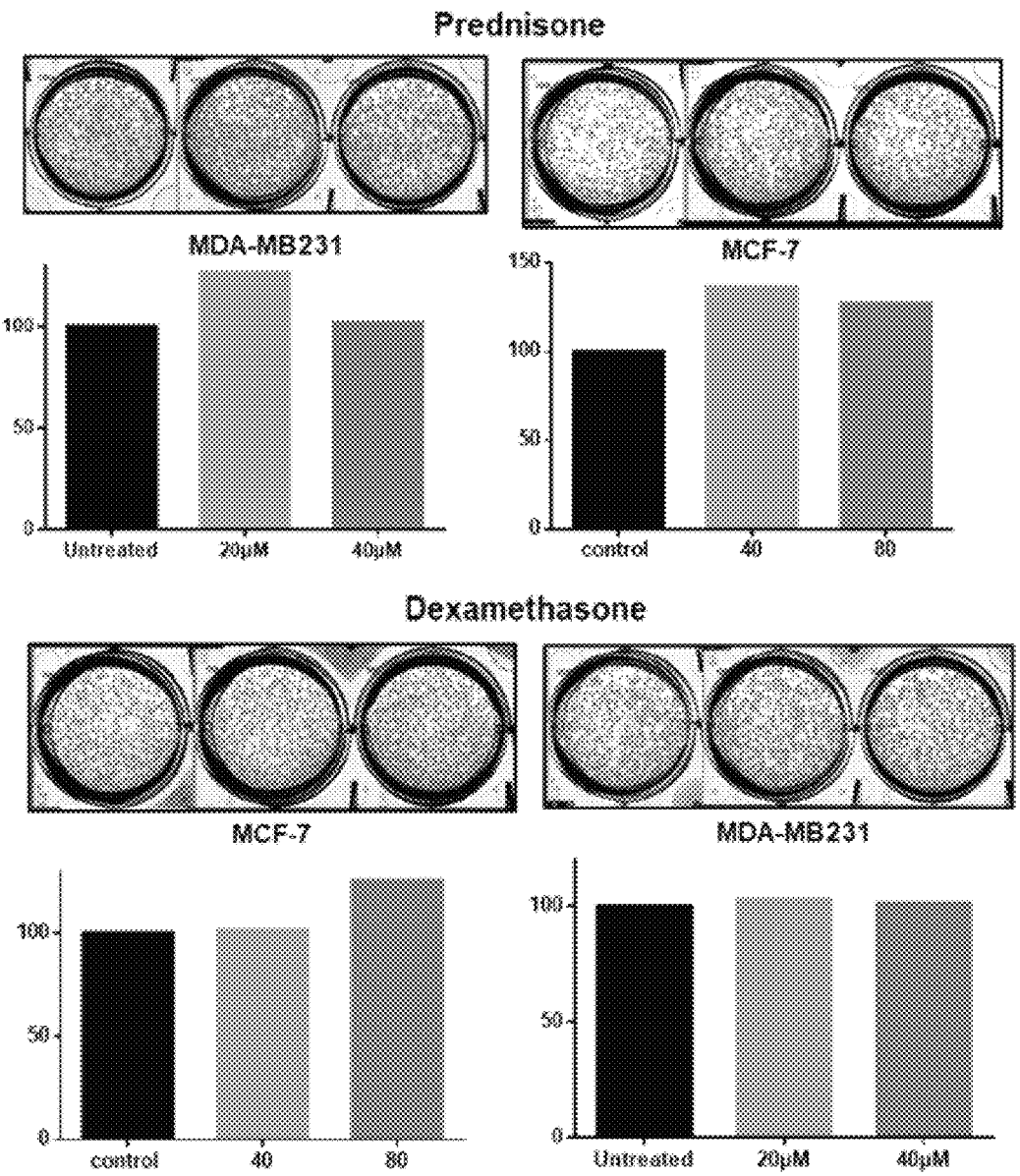

FIG. 3 illustrates an effect of ciclesonide on mammosphere formation, wherein MCF-7 cells and MDA-MB-231 cells were cultured under a mammosphere formation condition for 7 days, FIG. 3A illustrates an effect of ciclesonide on the formation of MCF-7 cell-derived mammospheres wherein primary mammospheres were cultured along with ciclesonide (5 μM or 10 μM) or DMSO, FIG. 3B illustrates an effect of ciclesonide on the formation of mammospheres derived from MDA-MD-231 cells wherein the mammospheres were cultured along with ciclesonide (10 μM) or DMSO, MCF-7 cells and MDA-MBB-231 cells were treated with ciclesonide or DMSO for 7 days, and images were acquired using a microscope at a magnification of ×10, which show representative mammospheres (scale bar=100 μm), and FIG. 3C illustrates results of examining effects of prednisone and dexamethasone (20 μM to 80 μM) on the formation of mammospheres derived from MCF-7 cells or MDA-MB231 cells.

Figure 4A:
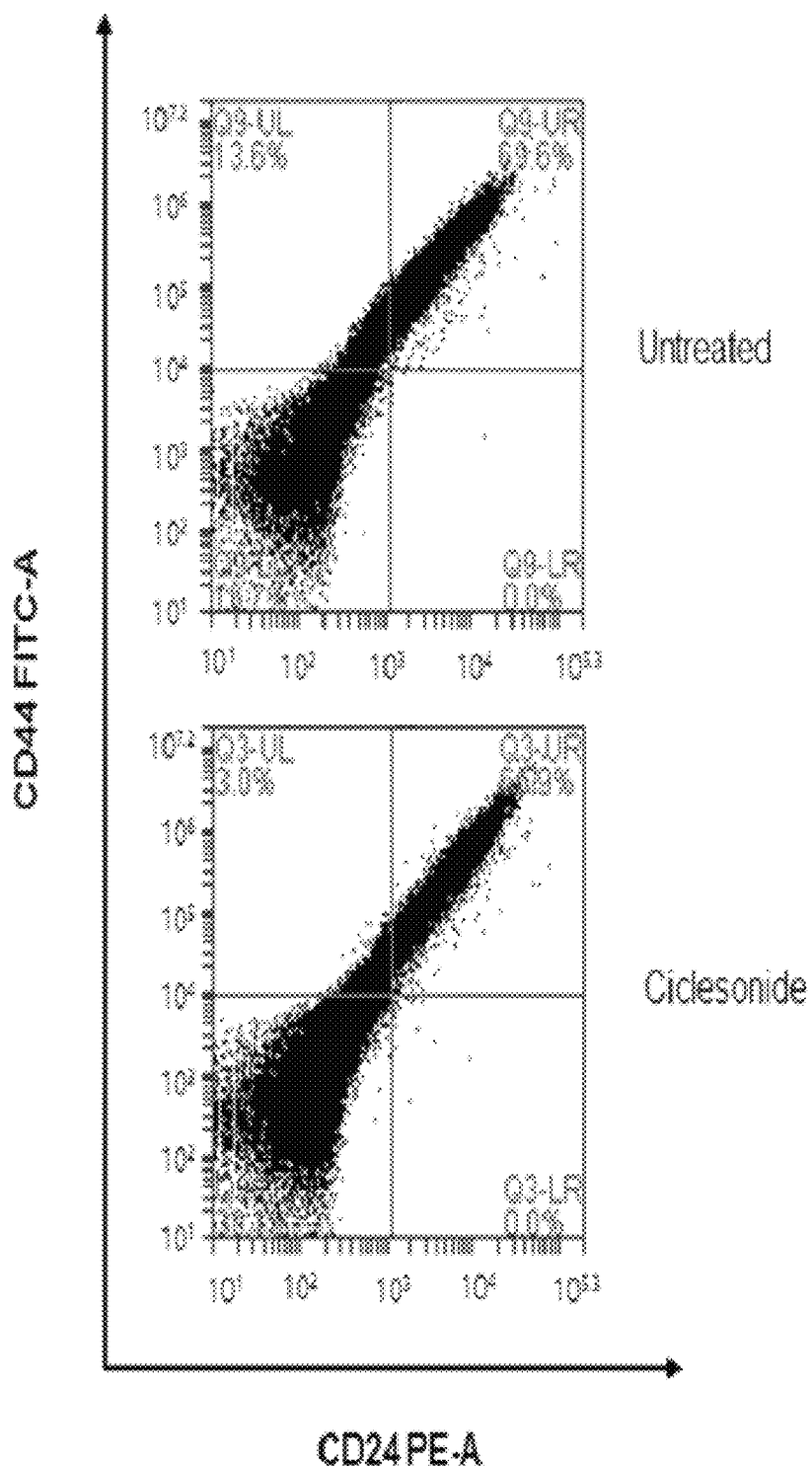
Figure 4B:
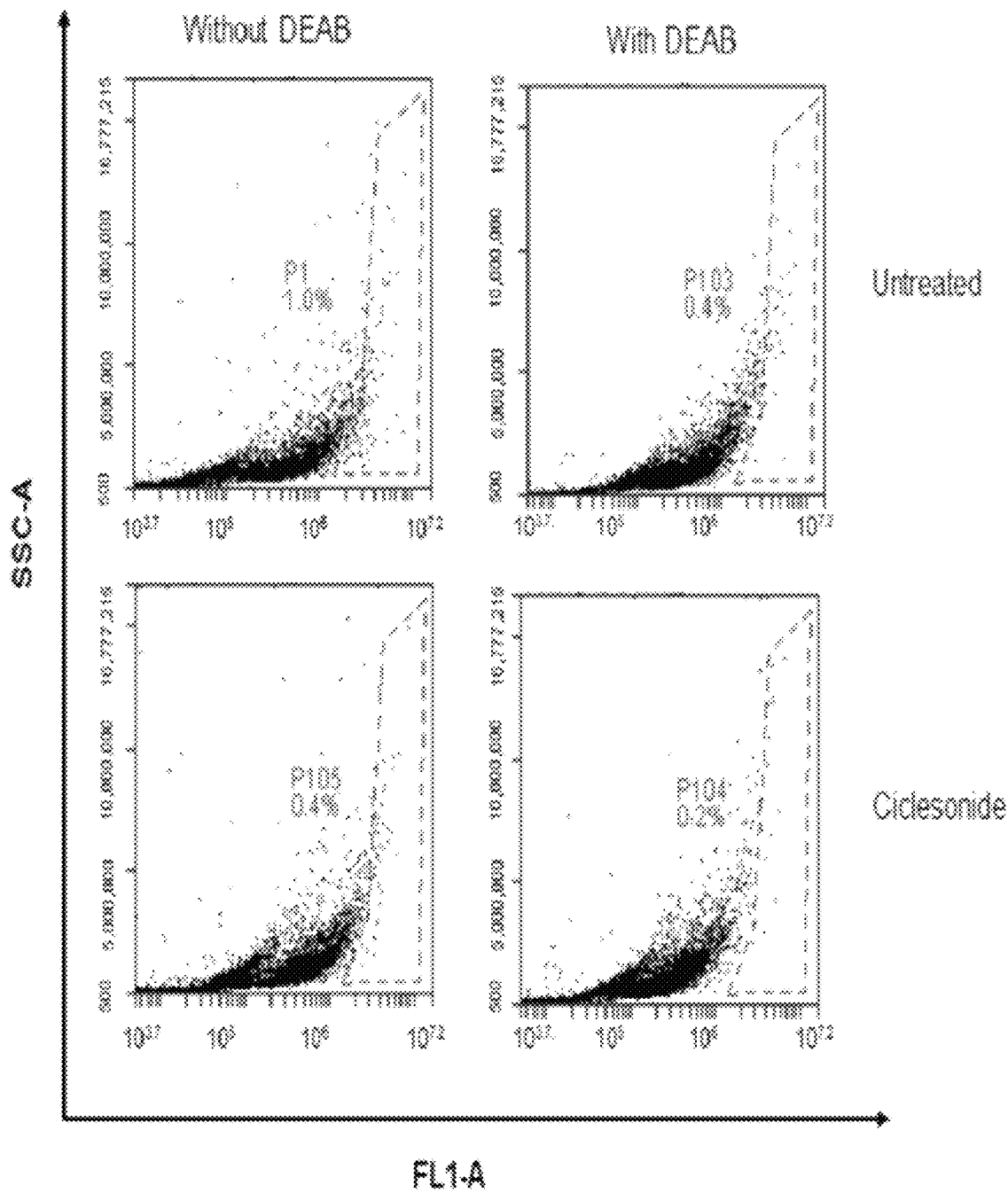

FIG. 4 illustrates an effect of ciclesonide on the expression of cancer stem cell markers in a breast cancer cell line, wherein FIG. 4A illustrates the effect of ciclesonide on the number of CD44+/CD24− cells in MDA-MB-231 cells wherein the ratio of CD44+/CD24− cells was measured in the MDA-MB-231 cells depending on whether or not to be treated with ciclesonide, for FACS analysis, 100,000 cells were obtained, and gating was based on a control antibody, and FIG. 4B illustrates the effect of ciclesonide on ALDH-positive cell population wherein MDA-MB-231 cells were treated with ciclesonide (10 μM) or DMSO for 2 days, followed by ALDEFLUOR analysis and FACS analysis, the right panel shows ALDH-positive cells treated with DEAB, which is an ALDH inhibitor, as a negative control, and the left panel shows ALDH-positive cells not treated with DEAB, and the ALDH-positive population was marked on the box.

Figure 5A:
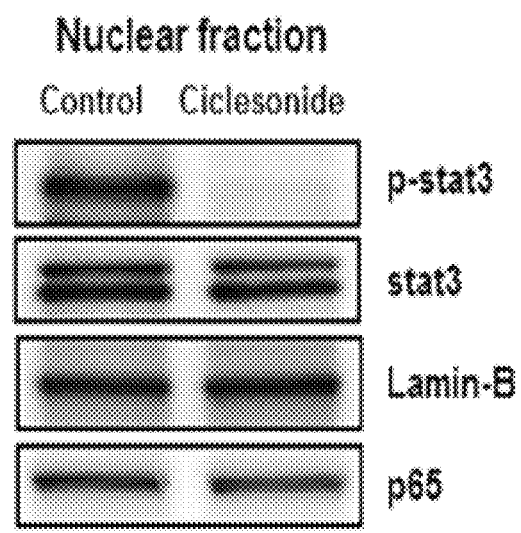
Figure 5B:
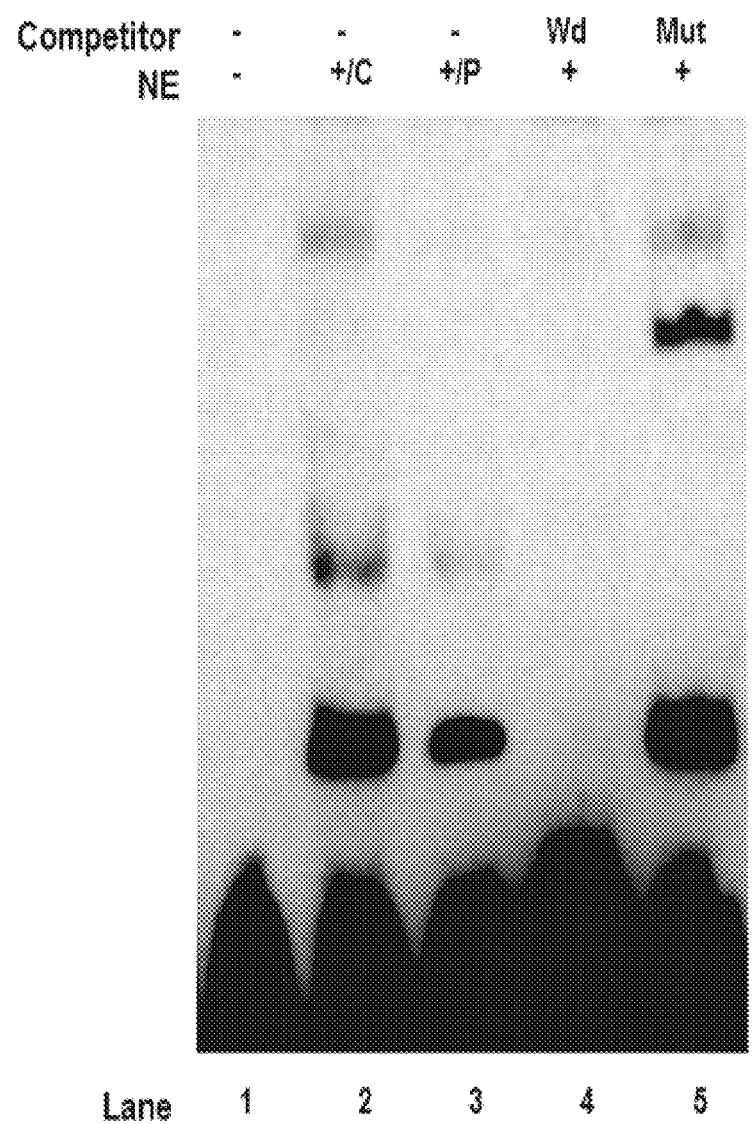
Figure 5C:
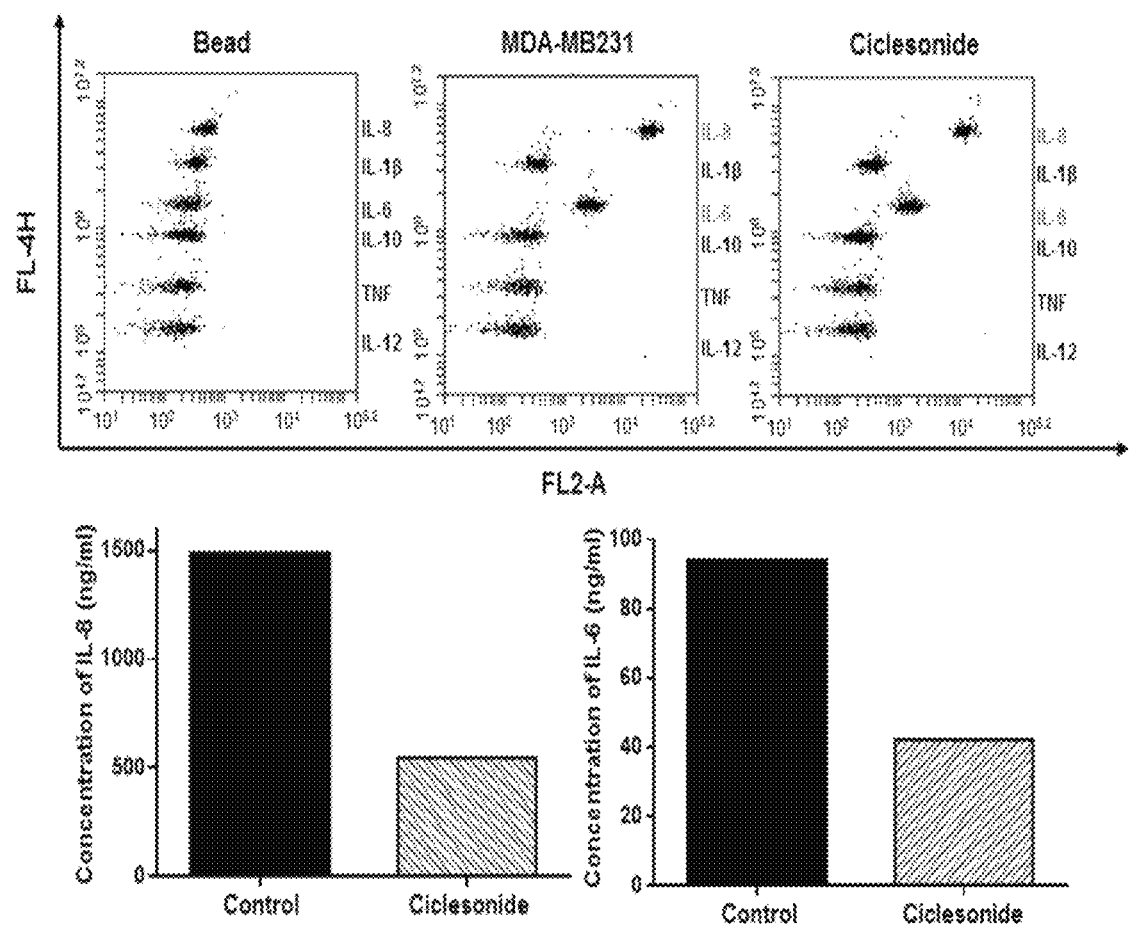

FIG. 5 illustrates an effect of ciclesonide on the STAT3 signaling pathway in mammospheres, wherein FIG. 5A illustrates the effect of ciclesonide on the STAT3 signaling pathway in mammospheres wherein nucleic protein expression and activation of STAT3 and NF-kB were measured with antibodies against pSTAT3, STAT3, P65 and lamin B in the mammospheres, and ciclesonide reduced the level of nuclear pSTAT3 protein in the mammospheres, FIG. 5B illustrates electrophoretic mobility shift assay (EMSA) results of mammosphere nuclear lysates derived from MDA-MB-231 cells treated with ciclesonide wherein the nuclear lysates were cultured with a biotin-labeled Stat3 probe and separated by 6% PAGE, Lane 1: probe alone; lane 2: probe+nuclear extract; lane 3: probe+ciclesonide-treated nuclear extract; lane 4: self-competitive; and lane 5: nuclear extract cultured with a mutant STAT3 probe, and the ciclesonide reduced DNA/STAT3 interactions in the mammosphere nuclear lysates, and FIG. 5C illustrates results of analyzing human inflammatory cytokines of tumors treated with ciclesonide or DMSO, wherein the inflammatory cytokines were measured using a BD cytometric bead array (CBA) human inflammatory cytokines kit, and CBA analysis was performed using antibodies against IL-6, IL-8, IL-10, IL-12, IL-1β, and TNF.

Figure 6A:
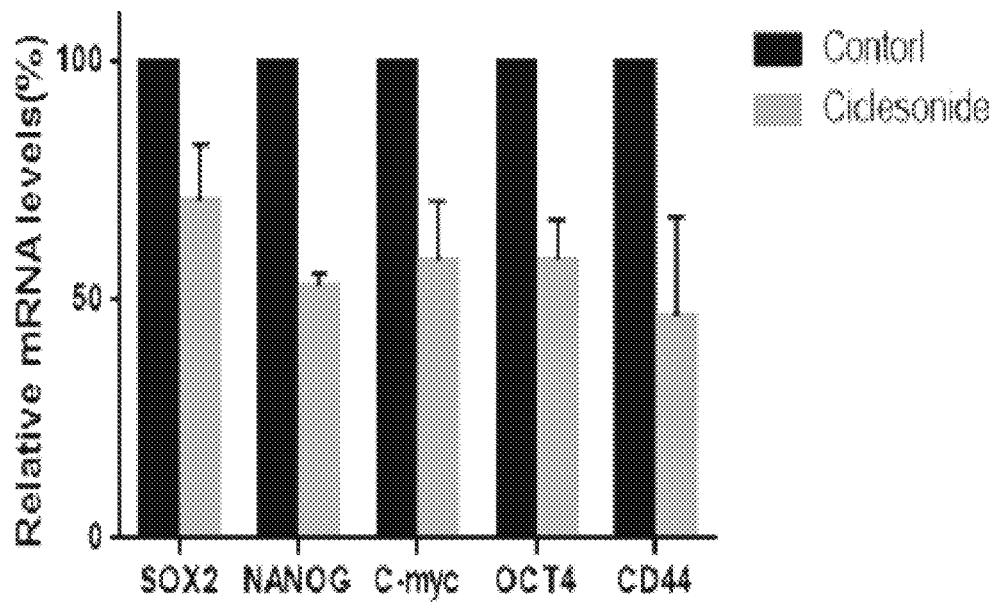
Figure 6B:
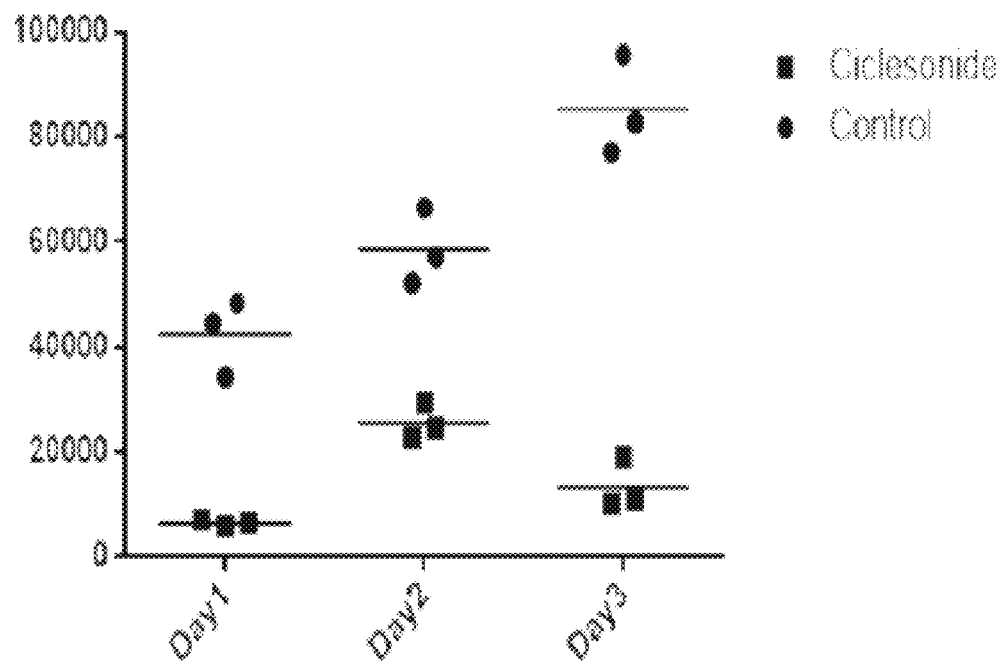

FIG. 6 illustrates an effect of ciclesonide on breast stem cell load in breast cancer, wherein FIG. 6A illustrates results of analyzing transcriptional expression levels of the Nanog, Sox2, C-myc, Oct4, and CD44 genes, which are CSC markers, by real-time PCR (RT-PCR) using CSC marker-specific primers in ciclesonide-treated mammospheres and DMSO-treated mammospheres, and β-actin was used as an internal control, and FIG. 6B illustrates the effect of ciclesonide on mammosphere growth wherein ciclesonide inhibits the growth of mammospheres, mammospheres having been treated with ciclesonide or DMSO for 2 days were separated into single cells and plated in 6 cm dishes at the same density. 24 hours after plating, the cells were counted, on days 2 and 3, the cells were counted three times, and plotted as mean values, and the data was expressed as the mean±SD for the three independent experimental results. *$p<0.05$ vs. DMSO-treated control.

Figure 7A:
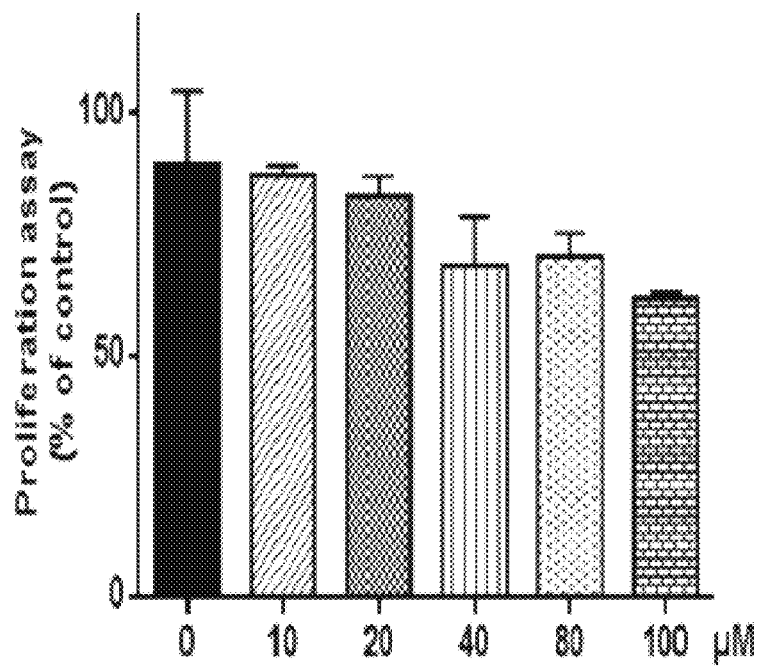
Figure 7B:
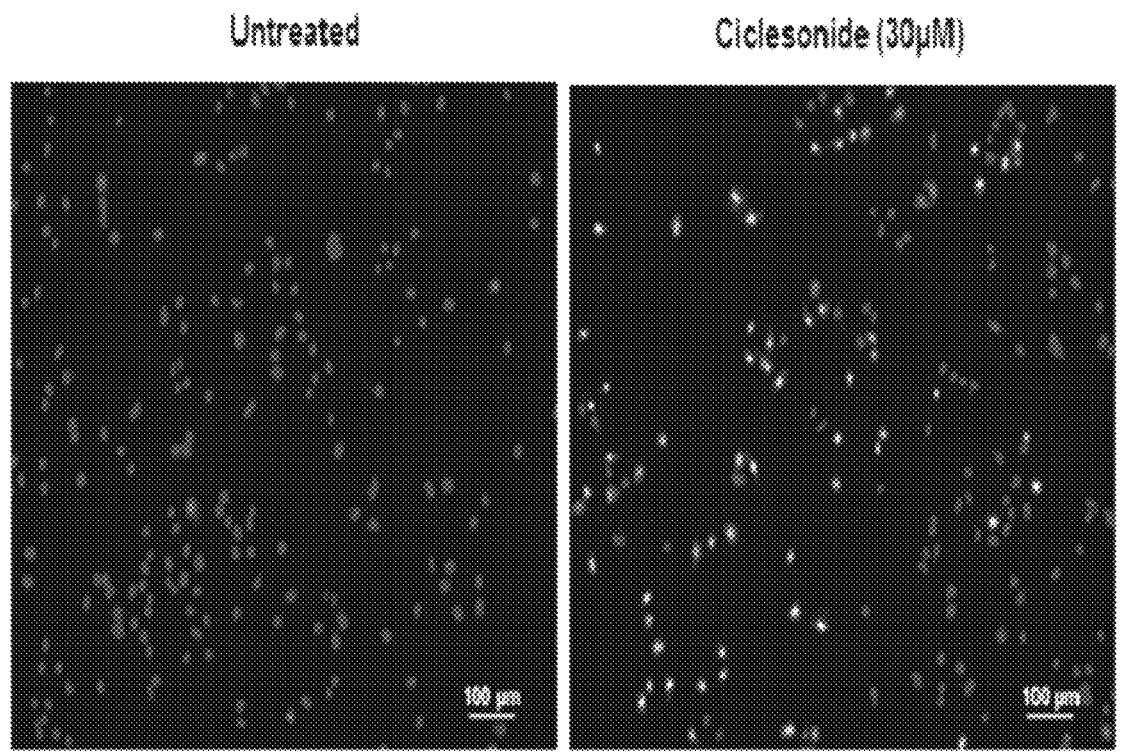
Figure 7C:
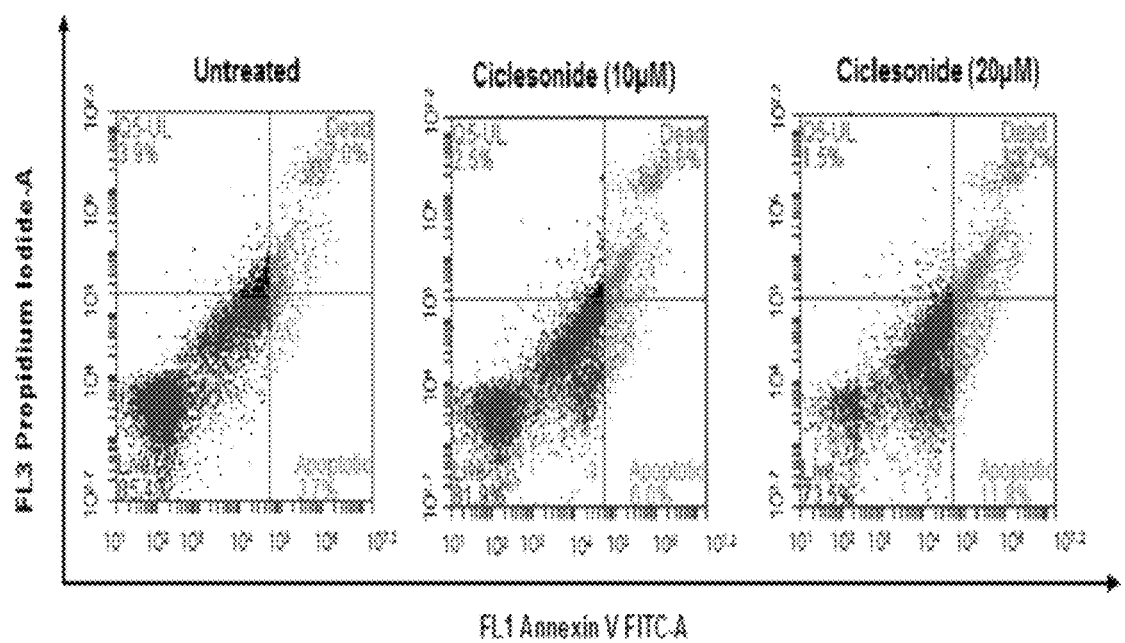
Figure 7D:
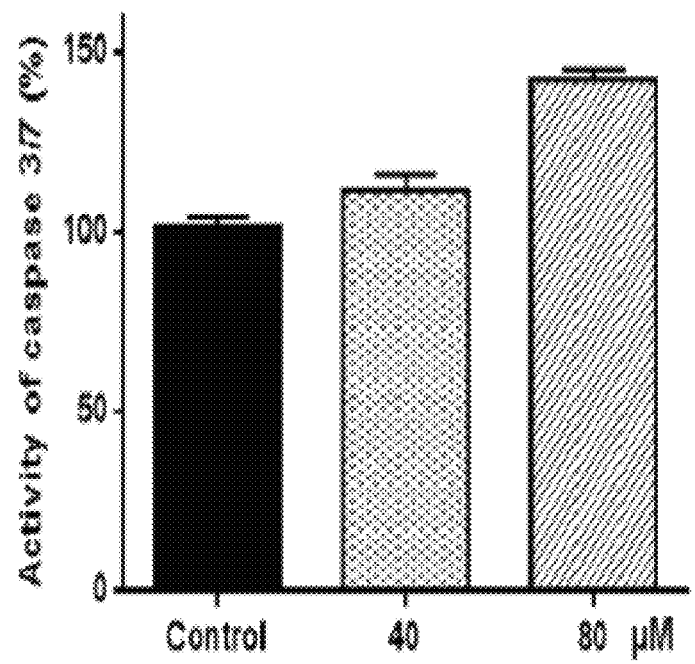
Figure 7E:
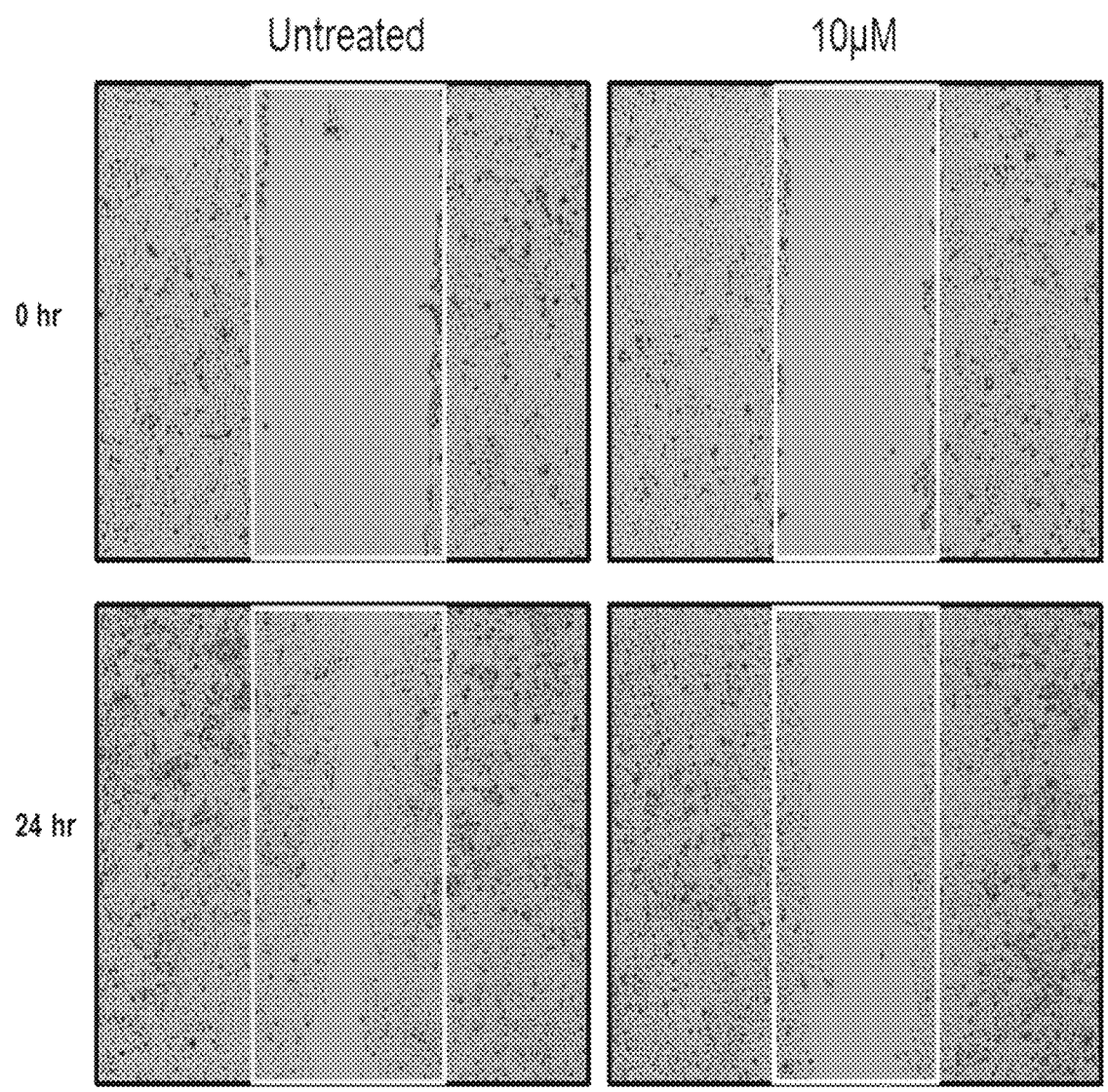
Figure 7F:
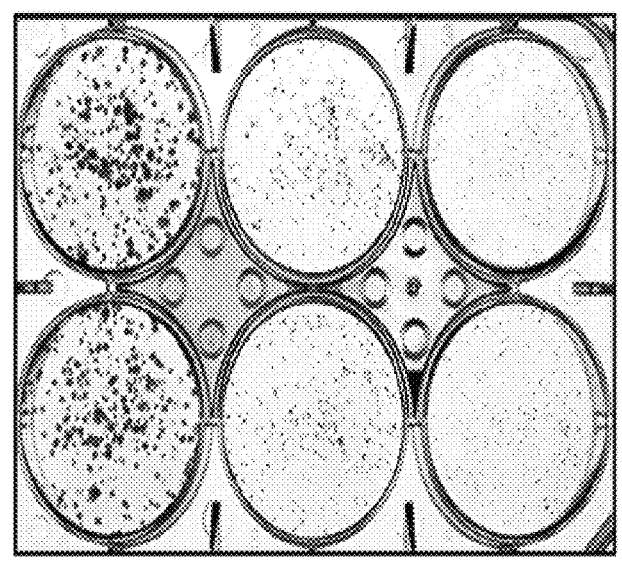
Figure 7F:
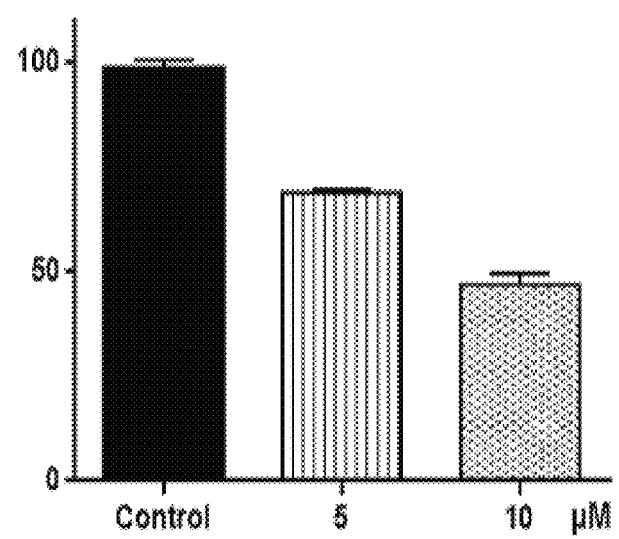

FIG. 7 illustrates the inhibition of various cancer characteristics by ciclesonide in a lung cancer cell line, wherein FIG. 7A illustrates the survival rate of ciclesonide for A549 lung cancer cells, A549 cells were treated with ciclesonide at increasing concentrations for 48 hours, and an antiproliferative effect of ciclesonide was measured by MTS assay, FIG. 7B illustrates results of analyzing apoptotic cells by fluorescence staining wherein nuclei of lung cancer cells were stained with Hoechst 33258 (at a magnification of 100×), FIG. 7C illustrates an effect of ciclesonide on apoptosis of lung cancer cells wherein A549 cells were treated with ciclesonide for 24 hours, and apoptotic cells were analyzed by FACS using an annexin V-PI staining kit, FIG. 7D illustrates results of analyzing caspase 3/7 activity in A549 cells by using a Caspase-Glo 3/7 kit, FIG. 7E illustrates an effect of ciclesonide on the migration potential of human lung cancer cells wherein wound healing of A549 cells were photographed at 0 hours and 18 hours depending on whether or not to be treated with ciclesonide, and FIG. 7F illustrates an effect of ciclesonide on colony formation in human lung cancer cells wherein the dissociated 1,000 A549 cells were inoculated into a 6-well plate and treated with ciclesonide or DMSO at indicated concentrations for 7 days, representative images of colonies were recorded, and the displayed data was expressed as the mean±SD for the three independent experimental results. *p<0.05 vs. DMSO-treated control.

Figure 8A:
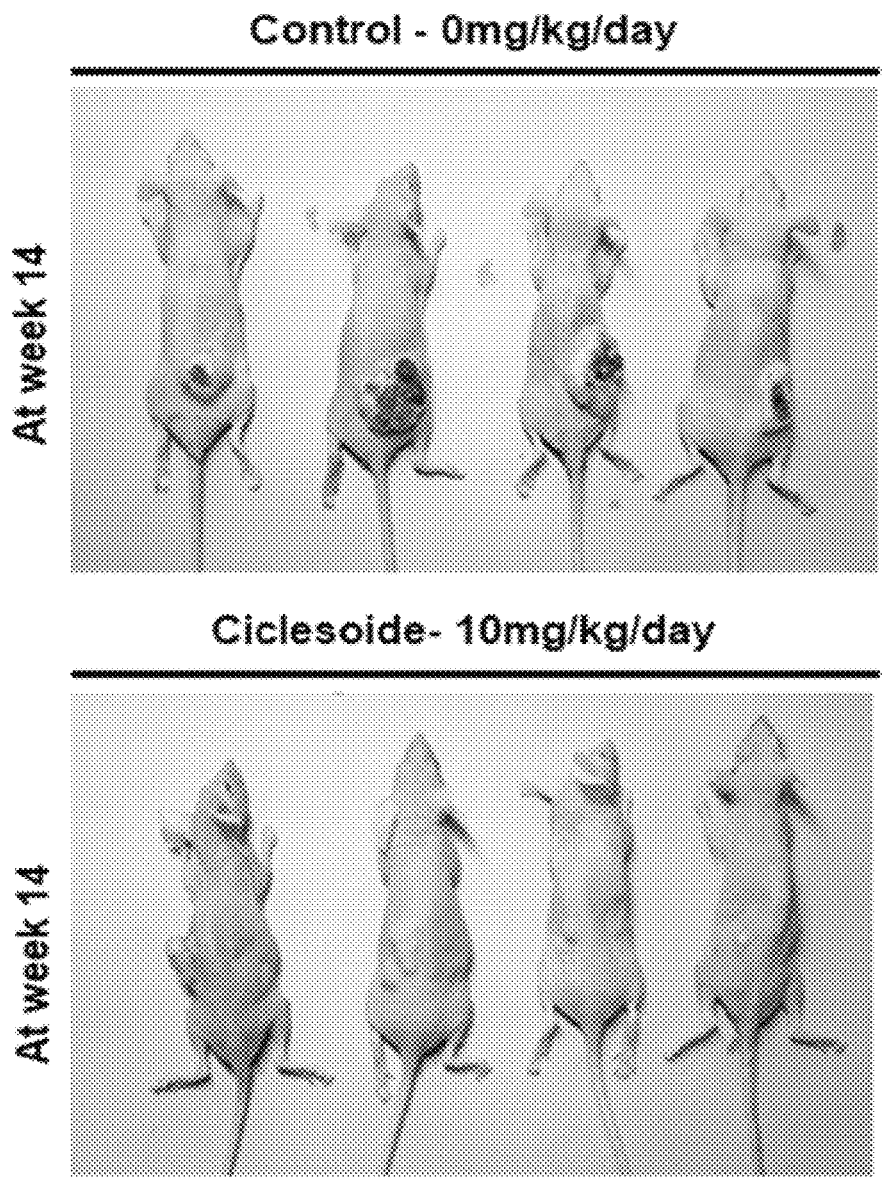
Figure 8B:
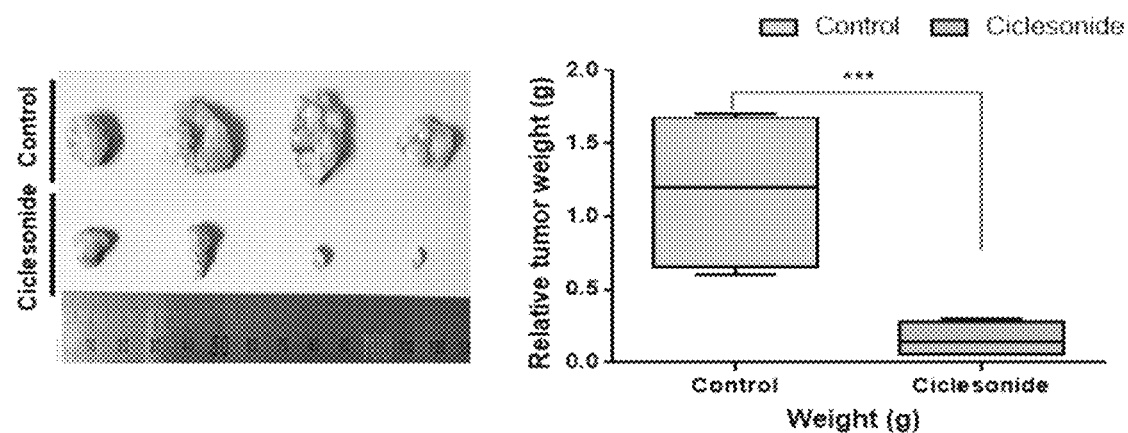
Figure 8C:
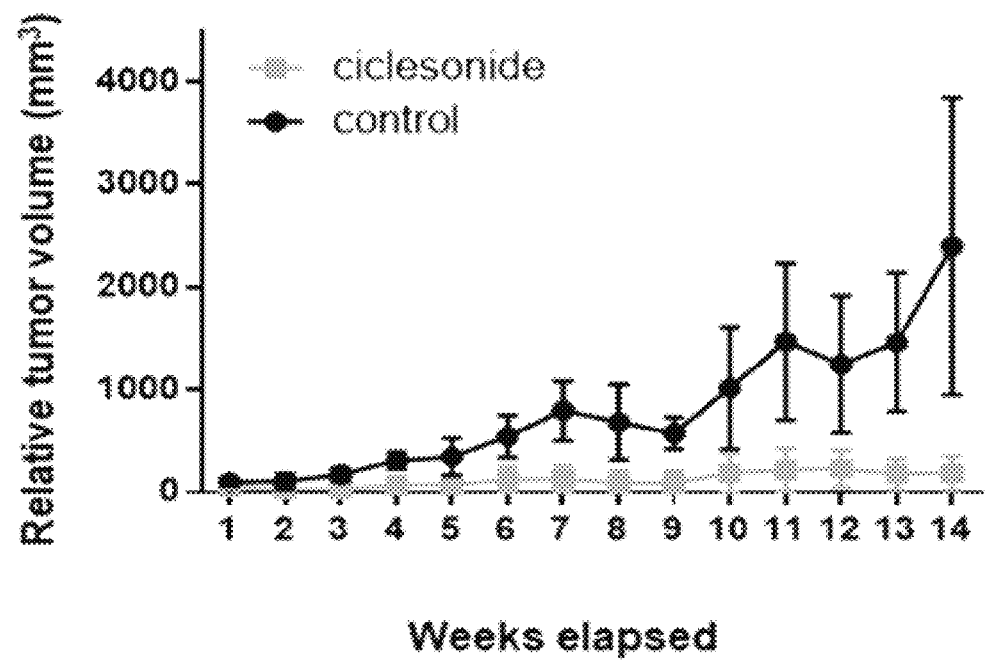

FIG. 8 illustrates an effect of ciclesonide on tumor growth in a xenograft model in which lung cancer cells were transplanted, wherein 5,000,000 cells were injected into subcutaneous tissues of immunodeficient NOD-SCID male nude mice, FIG. 8A illustrates an effect of ciclesonide on tumor growth in immunodeficient nude mice producing A549 cells, a dose of the drug used was 10 mg/kg, FIG. 8B illustrates an effect of ciclesonide on tumor weight wherein the tumor weight was measured after treatment, FIG. 8C illustrates tumor volume measured using calipers twice a week and calculated by (width×length$^2$)/2 wherein the tumor growth curve was monitored during the experimental period, and

*p<0.05 compared to a control, representative images were captured at the end of 14 weeks of treatment, and the results are shown for a vehicle-treated control and ciclesonide-treated mice.

Figure 9A:
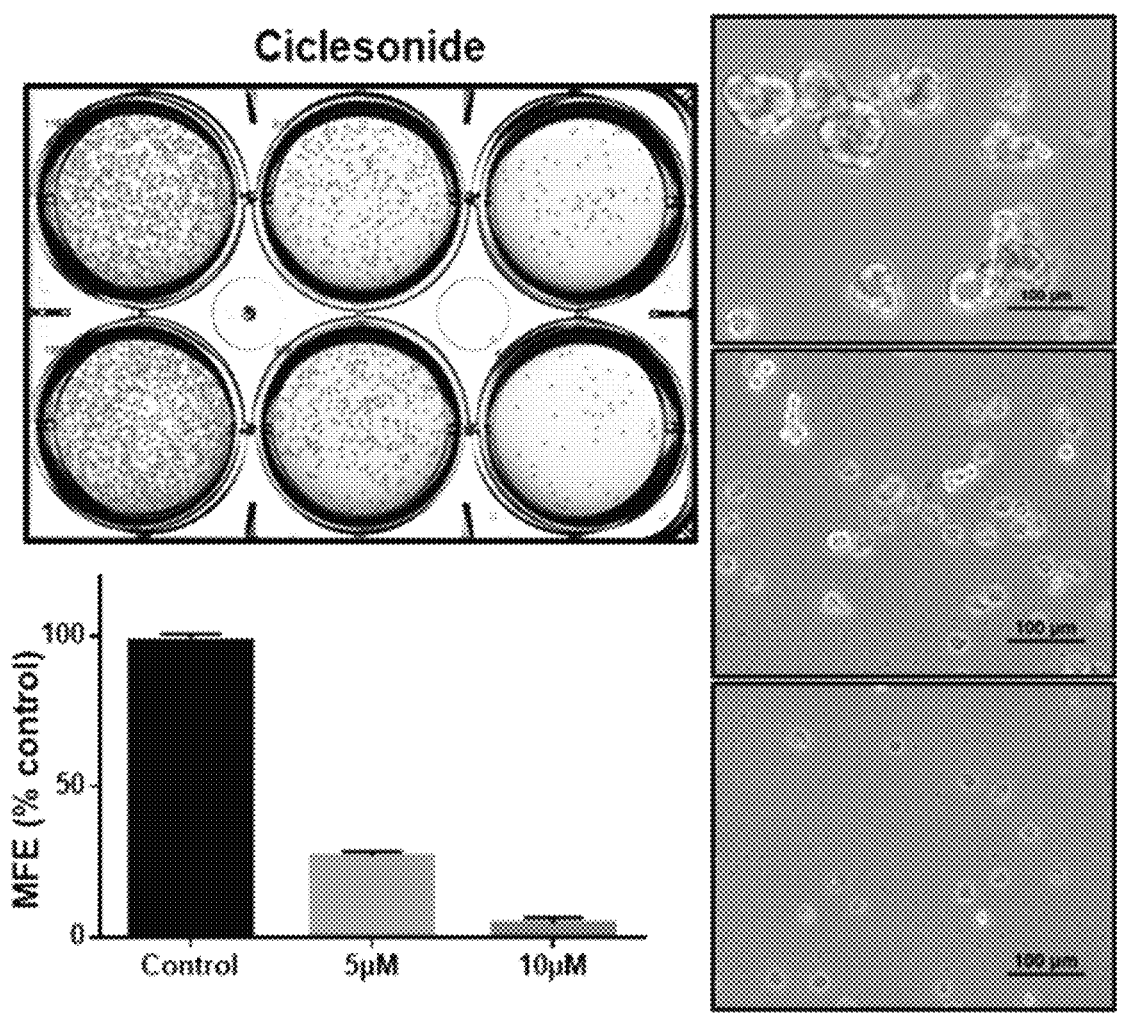
Figure 9B:
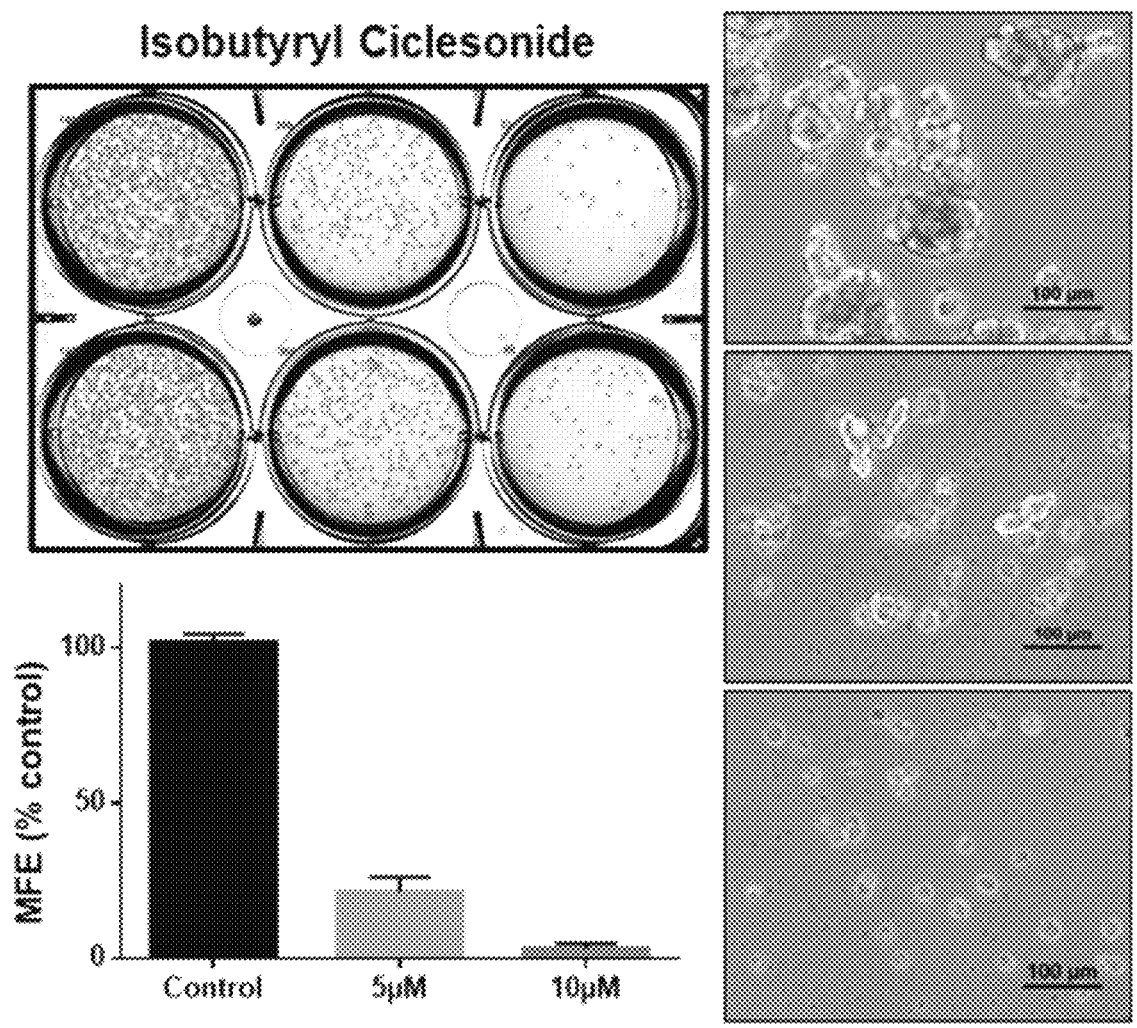
Figure 9C:
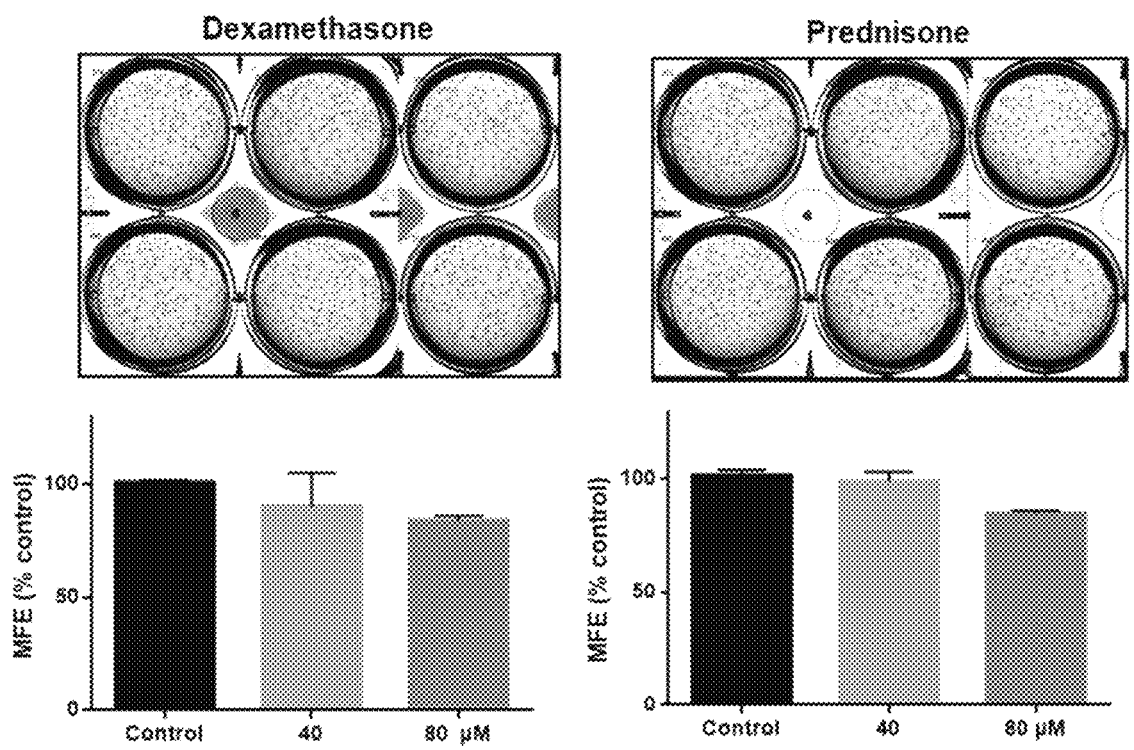

FIG. 9 illustrates an effect of ciclesonide on tumorsphere formation, wherein A549 cells were cultured under a tumorsphere formation condition for 7 days, FIG. 9A illustrates the effect of ciclesonide on the formation of tumorspheres derived from A549 cells, primary tumorspheres were cultured along with ciclesonide (5 μM and 10 μM) or DMSO for 7 days, FIG. 9B illustrates an effect of isobutyryl ciclesonide, which is an activated form of ciclesonide, on the formation of tumorspheres derived from A549 cells, FIG. 9C illustrates effects of prednisone and dexamethasone, which are glucocorticoids, on the formation of tumorspheres derived from A549 cells, primary tumorspheres were cultured along with prednisone and dexamethasone (40 μM and 80 μM) or DMSO for 7 days, images were acquired using a microscope at a magnification of ×10, which show representative tumorspheres (scale bar=100 μm).

Figure 10:
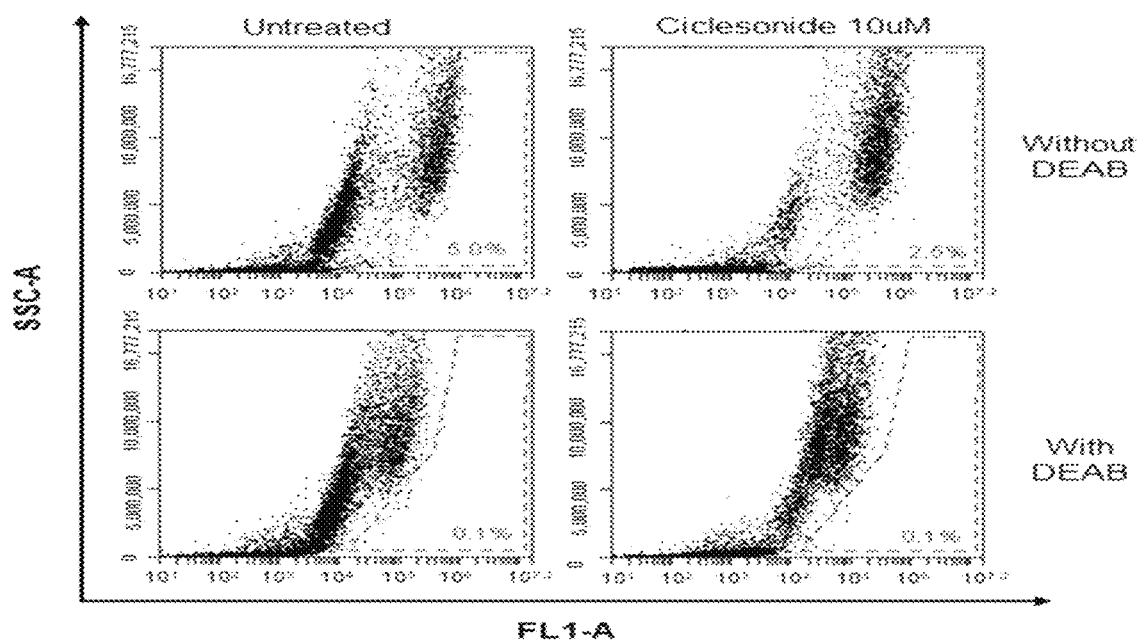

FIG. 10 illustrates an effect of ciclesonide on ALDH-positive cell population, wherein A549 cells were treated with ciclesonide or DMSO for 2 hours, followed by ALDEFLUOR analysis and FACS analysis, the lower panel shows ALDH-positive cells treated with DEAB, which is an ALDH inhibitor, and the upper panel shows ALDH-positive cells not treated with DEAB, and the ALDH-positive population was marked on the box.

Figure 11A:
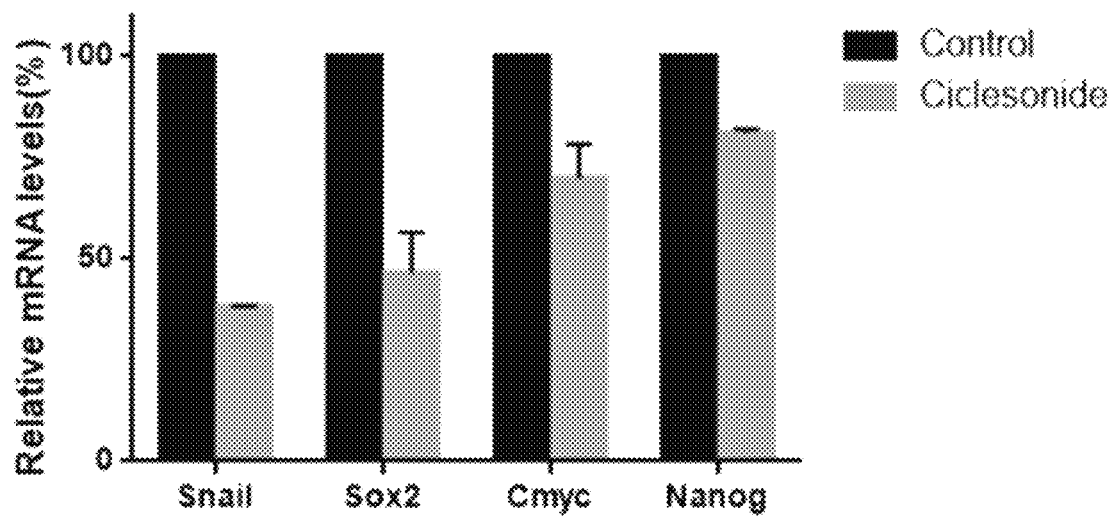
Figure 11B:
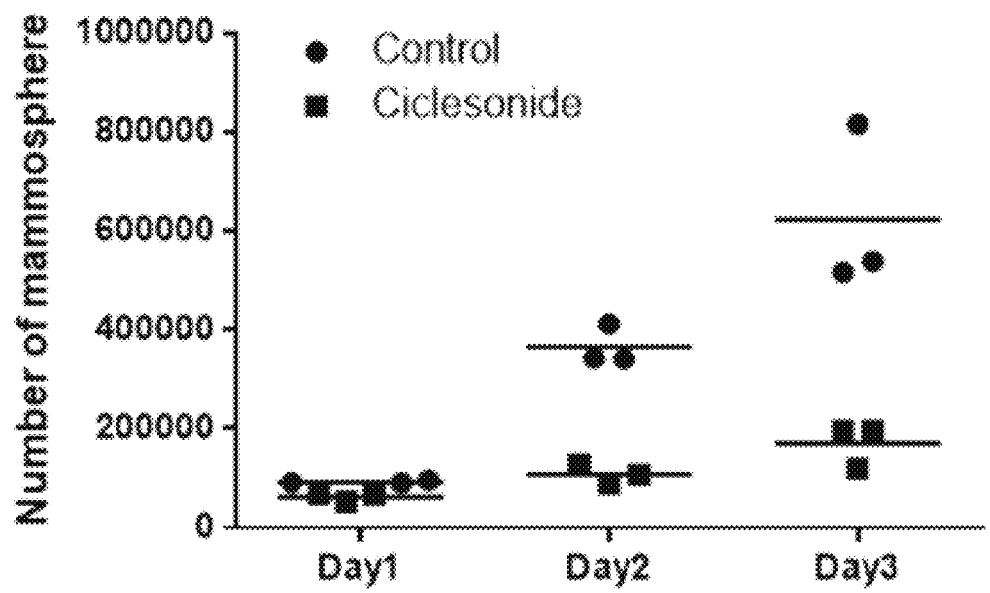
Figure 12:
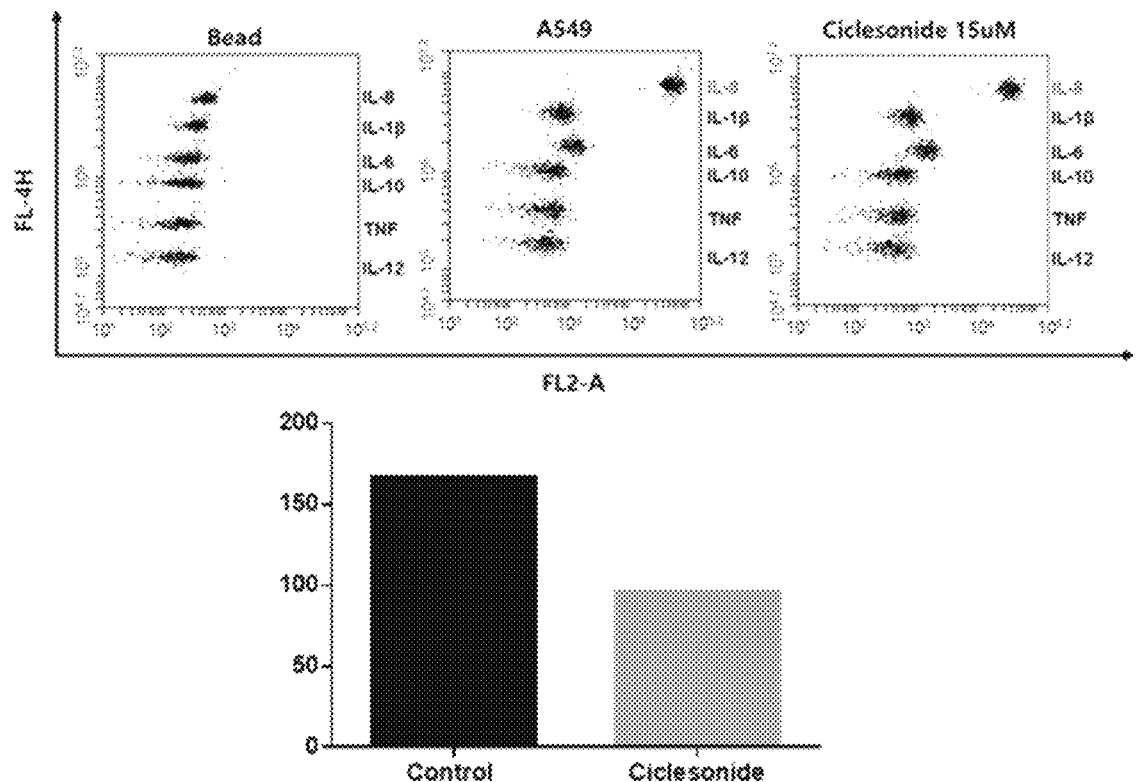

FIG. 11 illustrates an effect of ciclesonide on cancer stem cell load in lung cancer, wherein FIG. 11A illustrates results of analyzing transcriptional expression levels of the Nanog, Sox2, C-myc, and Snail genes, which are CSC markers, by RT-PCR using CSC marker-specific primers in ciclesonide-treated tumorspheres and DMSO-treated tumorspheres, and β-actin was used as an internal control, FIG. 11B illustrates the effect of ciclesonide on tumorsphere formation wherein ciclesonide inhibits the growth of tumorspheres, tumorspheres having been treated with ciclesonide or DMSO for 2 days were separated into single cells and plated in 6 cm dishes at the same density, 24 hours after plating, the cells were counted, on days 1, 2, and 3, the cells were counted three times, and plotted as mean values, and the data was expressed as the mean±SD for the three independent experimental results. *p<0.05 vs. DMSO-treated control; and FIG. 12 illustrates an effect of ciclesonide on a protein level of extracellular IL-8 in tumorspheres.

The drawing shows results of analyzing human inflammatory cytokines of tumors treated with ciclesonide or DMSO, the inflammatory cytokines were measured using a BD cytometric bead array (CBA) human inflammatory cytokines kit, and CBA analysis was performed using antibodies against IL-6, IL-8, IL-10, IL-12, IL-1β, and TNF.

BEST MODE

The inventors of the present invention examined whether the growth of cancer stem cells was inhibited using various compounds as cancer stem cell inhibitor candidates, and confirmed that, thereamong, ciclesonide selectively inhibited breast cancer stem cells and lung cancer stem cells. Ciclesonide is known to be an FDA-approved asthma therapeutic agent, but the inventors of the present invention first confirmed that ciclesonide inhibited the growth of breast cancer stem cells and selectively inhibited the STAT3 signaling pathway in breast cancer-derived mammospheres compared to MCF-7 bulk cells. In addition, they confirmed that tumor growth was effectively inhibited using a mouse xenograft model. Accordingly, the inventors of the present invention confirmed that ciclesonide inhibited the growth of cancer stem cells including breast cancer stem cells and lung cancer stem cells by targeting cancer stem cells (CSCs), and could be used for the treatment of cancer including breast cancer and lung cancer, and thus completed the present invention.

According to an embodiment of the present invention, there is provided a composition for inhibiting the growth of a cancer stem cell, which includes ciclesonide represented by Formula 1 below or a pharmaceutically acceptable salt thereof as an active ingredient.

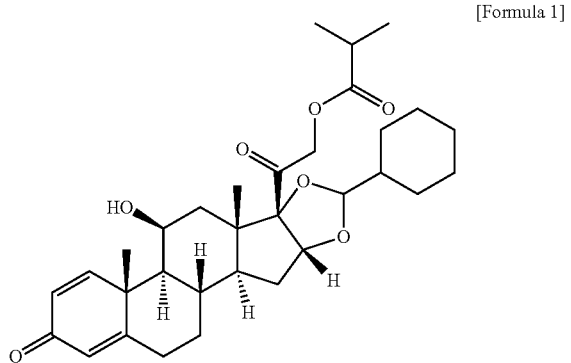

[Formula 1]

In the present invention, the ciclesonide is known to be an asthma therapeutic agent, but it was first confirmed by the inventors of the present invention that ciclesonide inhibited the growth of a breast cancer stem cell and a lung cancer stem cell.

The term "cancer" as used herein refers to or describes the physiological condition of a mammal that is generally characterized by unregulated cell growth. The term "cancer" as used herein refers to a condition in which cells abnormally overgrow due to dysfunction in the regulation of normal division, differentiation, and apoptosis, thus invading into the surrounding tissues and organs to thereby form cell aggregates and destroy or transform existing structures.

The term "cancer stem cell" as used herein refers to an undifferentiated cell capable of differentiating into various cancer cells, and the cancer may be colon cancer including colorectal cancer and rectal cancer, breast cancer, uterine cancer, cervical cancer, ovarian cancer, prostate cancer, brain tumor, head and neck carcinoma, melanoma, myeloma, leukemia, lymphoma, gastric cancer, lung cancer, pancreatic cancer, liver cancer, esophageal cancer, small intestine tumor, anal cancer, fallopian tube carcinoma, endometrial carcinoma, vaginal carcinoma, vulva carcinoma, Hodgkin's disease, bladder cancer, renal cancer, ureteral cancer, renal cell carcinoma, kidney pelvic carcinoma, bone cancer, skin cancer, head cancer, skin melanoma, intraocular melanoma, endocrine adenocarcinoma, thyroid cancer, parathyroid cancer, adrenal cancer, soft tissue sarcoma, urethral cancer, penis cancer, central nervous system (CNS) tumors, primary CNS lymphoma, spinal cord tumor, brainstem glioma, or pituitary adenoma. The cancer stem cell may be, but is not limited to, a breast cancer stem cell or a lung cancer stem cell.

The term "breast cancer stem cell" as used herein refers to an undifferentiated cell capable of differentiating into breast cancer cells.

The term "lung cancer stem cell" as used herein refers to an undifferentiated cell capable of differentiating into lung cancer cells.

The expression "inhibiting the growth of a breast cancer stem cell" is meant to include inhibition of the maintenance of a breast cancer stem cell, inhibition of the malignancy of a breast cancer stem cell, and inhibition of the migration and invasive activity of a breast cancer stem cell.

The expression "inhibiting the growth of a lung cancer stem cell" is meant to include inhibition of the maintenance of a lung cancer stem cell, inhibition of the malignancy of a lung cancer stem cell, and inhibition of the migration and invasive activity of a lung cancer stem cell.

In one embodiment of the present invention, to examine whether ciclesonide is capable of inhibiting the growth of a breast cancer stem cell, primary mammospheres derived from MCF-7 cells or MDA-MB-231 cells were treated with ciclesonide, and from the results, it was confirmed that ciclesonide inhibited the formation of the primary mammospheres derived from the breast cancer cell lines, and particularly, the number of mammospheres derived from MCF-7 cells or MDA-MB-231 cells, which are breast cancer lines, was reduced by 90% and the size of mammospheres was also reduced (see FIGS. 3A and 3B). In contrast, it was confirmed that prednisone and dexamethasone, which are glucocorticoids, were unable to inhibit the growth of breast cancer stem cells even at a high concentration, i.e., 80 μM (see FIG. 3C).

In addition, in another embodiment of the present invention, to examine whether ciclesonide is capable of inhibiting the growth of a lung cancer stem cell, primary tumorspheres derived from A549 cells were treated with ciclesonide, and from the results, it was confirmed that ciclesonide inhibited the formation of the primary tumorspheres derived from a lung cancer cell line, and particularly, the number of the tumorspheres derived from A549 cells, which are lung cancer cells, was reduced by 90%, and the size of the tumorspheres was also reduced (see FIG. 9A). In addition, as a result of treatment with isobutyryl ciclesonide, which is an activated form of ciclesonide, it was confirmed that isobutyryl ciclesonide exhibited a lung cancer stem cell inhibitory activity at concentrations of 5 μM and 10 μM. In contrast, prednisone and dexamethasone, which are glucocorticoids, did not exhibit a lung cancer stem cell inhibitory activity even at a concentration of 80 μM (see FIG. 9C).

Accordingly, the compound of the present invention may (i) inhibit the formation of breast cancer-derived mammospheres, (ii) inhibit the proliferation of breast cancer-derived mammospheres, (iii) inhibit the formation of lung cancer-derived tumorspheres, or (iv) inhibit the proliferation of lung cancer-derived tumorspheres.

In one embodiment of the present invention, the breast cancer stem cell may express at least one self-renewal gene selected from Nanog, C-myc, Oct4, Sox2, and CD44, and the lung cancer stem cell may express at least one self-renewal gene selected from Nanog, Sox2, C-myc, and Snail.

In one embodiment of the present invention, it was confirmed that ciclesonide inhibited the expression of self-renewal genes such as Nanog, C-myc, Oct4, Sox2, and CD44, which are known to be characteristically expressed in breast cancer stem cells (see FIG. 6A), and inhibited the STAT3 signaling pathway involved in mammosphere formation of breast cancer stem cells (see FIGS. 5A and 5B). It was also confirmed that ciclesonide inhibited the production of IL-6 and IL-8, which are known to be involved in mammosphere formation of breast cancer stem cells (see FIG. 5C). Accordingly, it was confirmed that the compound was able to inhibit the growth of a breast cancer stem cell.

In addition, it was confirmed that ciclesonide inhibited the expression of self-renewal genes such as Nanog, Sox2, C-myc, and Snail, which are known to be characteristically expressed in lung cancer stem cells (See FIG. 11A), and inhibited the production of IL-8, which is known to be involved in tumorsphere formation of lung cancer stem cells (see FIG. 12). Accordingly, it was confirmed that the compound was able to inhibit the growth of a lung cancer stem cell.

The composition of the present invention may be used as a pharmaceutical composition or a food composition.

When used as a pharmaceutical composition, the composition of the present invention may include the ciclesonide or a pharmaceutically acceptable salt thereof.

The term "pharmaceutically acceptable salt" as used herein refers to all salts that possess a desired biological and/or physiological activity of the compound and minimally exhibit undesired toxicological effects. The pharmaceutically acceptable salt refers to a salt prepared according to a general method known in the art, and this general preparation method is known to those of ordinary skill in the art. In particular, the pharmaceutically acceptable salt includes, but is not limited to, salts derived from pharmacologically or physiologically acceptable inorganic and organic acids and bases.

For example, pharmaceutically acceptable base addition salts may be prepared from inorganic and organic bases. Salts derived from inorganic bases may include, but are not limited to, sodium salts, potassium salts, lithium salts, ammonium salts, calcium salts, and magnesium salts. Examples of salts derived from organic bases may include, but are not limited to, primary, secondary, and tertiary amines; substituted amines containing naturally occurring substituted amines; and salts of cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamine, theobromine, purine, piperazine, piperidine, and/or N-ethylpiperidine. In addition, other carboxylic acid derivatives, e.g., carboxylic acid amides including carboxamides, lower alkyl carboxamides, di(lower alkyl)carboxamide, and the like may also be included.

For example, pharmaceutically acceptable acid addition salts may be prepared from inorganic and organic acids. Salts derived from inorganic acids include hydrochloric acid, bromic acid, sulfuric acid, nitric acid, phosphoric acid, and the like. Salts derived from organic acids may include, but are not limited to, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and/or salicylic acid.

In the present invention, the pharmaceutical composition may include a pharmaceutically acceptable carrier or an additive. The term "pharmaceutically acceptable" as used herein refers to not inhibiting the activity of an active ingredient and not having a greater level of toxicity than a subject in need of application (treatment) can stand. The term "carrier" as used herein is defined as a compound that facilitates the addition of a compound into a cell or tissue.

The ciclesonide of the present invention may be administered alone or in combination with any suitable carrier or the like, and a dosage form thereof may be a single-dose or multi-dose preparation. The pharmaceutical composition may be a solid preparation or a liquid preparation. Examples of solid preparations include, but are not limited to, powders, granules, tablets, capsules, and suppositories. Examples of solid preparations may include, but are not limited to, carriers, flavoring agents, binders, preservatives, disintegrants, lubricants, and fillers. Examples of liquid preparations may include, but are not limited to, solutions such as water and a propylene glycol solution, suspensions, and emulsions, and these liquid preparations may be prepared by adding a suitable colorant, flavoring agent, stabilizer, tackifier, or the like. For example, powders may be prepared by simply mixing ciclesonide, which is the active ingredient of the present invention, with a suitable pharmaceutically acceptable carrier such as lactose, starch, microcrystalline cellulose, or the like. Granules may be prepared by mixing the ciclesonide of the present invention, a suitable pharmaceutically acceptable salt, and a suitable pharmaceutically acceptable binder such as polyvinylpyrrolidone, hydroxypropylcellulose, or the like, and then performing, on the resulting mixture, wet granulation using a solvent such as water, ethanol, isopropanol, or the like, or dry granulation using compressive force. In addition, tablets may be prepared by mixing the granules with a suitable pharmaceutically acceptable lubricant such as magnesium stearate, or the like, and then tableting the mixture using a tablet press.

The ciclesonide of the present invention may be administered depending on the condition of a disease to be treated and an individual in the form of an oral preparation, an injection (e.g., intramuscular injection, intraperitoneal injection, intravenous injection, infusion, subcutaneous injection, and implant), an inhalant, a nasal administration agent, a vaginal agent, a rectal administration agent, a sublingual agent, a transdermal agent, a topical agent, or the like, but the present invention is not limited thereto. The ciclesonide of the present invention may be formulated into a suitable dosage unit preparation including a pharmaceutically acceptable carrier, additive, or vehicle that is commonly used and non-toxic, depending on administration routes.

The pharmaceutical composition of the present invention may be administered at a daily dose of about 0.0001 mg/kg to about 10 g/kg, for example, about 0.001 mg/kg to about 1 g/kg. However, the dosage may vary depending on the degree of purification of the mixture, the condition of a patient (age, gender, body weight, or the like), severity of the condition being treated, and the like. For convenience, the pharmaceutical composition may be administered in multiple doses a day as needed.

When the composition of the present invention is used as a pharmaceutical composition, the amount of ciclesonide in the composition may be appropriately adjusted to an effective amount capable of exhibiting anti-inflammatory activity according to the symptoms of a disease, the progression of a symptom, the condition of a patient, and the like. For example, the amount of the ciclesonide may range from about 0.0001 wt %, particularly about 0.001 wt % to about 80 wt %, particularly about 50 wt %, with respect to a total weight of the composition, but the present invention is not limited thereto.

In addition, the ciclesonide of the present invention was confirmed to inhibit the growth (proliferation) of breast cancer cell-derived mammospheres, and thus may be used as a food composition for inhibiting the growth of a breast cancer stem cell. In addition, the ciclesonide of the present invention was confirmed to inhibit the growth (proliferation) of lung cancer cell-derived tumorspheres, and thus may be used as a food composition for inhibiting the growth of a lung cancer stem cell.

When used as a food composition, the composition of the present invention may include an acceptable supplementary food additive, and may further include a suitable carrier, excipient, and diluent that is commonly used in the preparation of foods.

The term "food" as used herein refers to a natural substance or a processed product that contains one or more nutrients, particularly a state directly edible through a certain processing process. In a general sense, the term "food" is used to encompass various foods, functional foods, beverages, food additives, and beverage additives. Examples of the food include various kinds of foods, beverages, gum, teas, vitamin complexes, functional foods, and the like. In addition, examples of the food of the present invention include, but are not limited to, special nutritional foods (e.g., crude oils and baby food), meat processed products, fish products, tofu, jellied foods, noodles (e.g., instant noodles and noodles), health supplements, food seasonings (e.g., soy sauce, soybean paste, red pepper paste, and mixed paste), sauces, confectionary (e.g., snacks), dairy products (e.g., fermented milk and cheese), other processed foods, kimchi, pickled foods (various fermented foods and pickled vegetables), beverages (e.g., fruit and vegetable beverages, soybean milk, fermented beverages, and ice creams), natural seasonings (e.g., ramen soup base), vitamin complexes, alcoholic beverages, liquors, and other health supplement foods. The functional foods, the beverages, the food additives, or the beverage additives may be prepared using general preparation methods.

The term "functional food" as used herein refers to a group of foods having added values provided by a physical, biochemical, or biotechnological method so that the corresponding food imparts or exhibits intended functions suitable for specific applications, or a processed food designed such that a composition of the food sufficiently imparts, in the body, body modulation functions regarding biological defense rhythm control, disease prevention and recovery, and the like, and particularly, the functional food may be a health functional food.

The term "health functional food" as used herein refers to foods prepared and processed in the form of tablets, capsules, powders, granules, liquids, pills, or the like by using raw materials or ingredients having useful functionality in the human body. The term "functionality" as used herein refers to controlling nutrients for the structure and functions of the human body or obtaining useful effects of hygienic purposes, such as psychological effects, and the like. The health functional food of the present invention may be prepared using a method commonly used in the art, and may be prepared by adding raw materials and ingredients commonly used in the art. In addition, the health functional food may be prepared into a form without limitation as long as the form is acceptable as a health functional food. The food composition of the present invention may be prepared into various types of preparations, and unlike general drugs, the food composition has no side effects that may occur during long-term administration of a drug because it uses foods as raw materials, and is highly portable. Therefore, the health functional food of the present invention may be taken as a supplement for enhancing an effect of inhibiting the growth of a breast cancer stem cell and a lung cancer stem cell.

In addition, the functional food may include a sitologically acceptable supplementary food additive, and may further include a suitable carrier, excipient, and diluent that is commonly used in the preparation of functional foods.

In addition, the amount of the ciclesonide in the food composition may range from about 0.00001 wt %, particularly about 0.1 wt % to about 80 wt %, particularly about 50 wt %, and more particularly about 40 wt %, with respect to a total weight of the food composition. When the food is a beverage, the amount of the ciclesonide may range from about 0.001 g, particularly about 0.01 g to 50 g, particularly about 10 g, and more particularly about 2 g, with respect to a total volume (100 ml) of the food, but the present invention is not limited thereto.

The food composition of the present invention may further include, in addition to the active ingredient, a sweetener, a flavoring agent, physiologically active ingredients, minerals, and the like. Sweeteners may be used in an amount that sweetens the food to a suitable extent, and may be natural or synthetic sweeteners. In particular, when a natural sweetener is used, the natural sweetener may be a sugar sweetener such as corn syrup solids, honey, sucrose, fructose, lactose, maltose, or the like. Flavoring agents may be used to enhance taste or flavor, and both natural and synthetic flavoring agents may be used. In particular, natural flavoring agents may be used. Natural flavoring agents may be used not only for the flavoring purpose, but also for the purpose of nutritional enhancement. Natural flavoring agents may be obtained from apples, lemons, citrus fruits, grapes, strawberries, peaches, and the like, or may be obtained from green tea leaves, Solomon's seal leaves, bamboo leaves, cinnamon leaves, chrysanthemum leaves, jasmine leaves, and the like. In addition, natural flavoring agents may be obtained from ginseng (red ginseng), bamboo shoots, aloe vera, ginkgo nuts, and the like. Natural flavoring agents may take the form of liquid concentrates or solid extracts. In some embodiments, synthetic flavoring agents may be used, and may be esters, alcohols, aldehydes, terpenes, and the like. Non-limiting examples of the physiologically active substances include catechins such as catechin, epicatechin, gallocatechin and epigallocatechin, and vitamins such as retinol, ascorbic acid, tocopherol, calciferol, thiamine, and riboflavin. As the minerals, calcium, magnesium, chromium, cobalt, copper, fluoride, germanium, iodine, iron, lithium, magnesium, manganese, molybdenum, phosphorus, potassium, selenium, silicon, sodium, sulfur, vanadium, zinc, and the like may be used.

In addition, the food composition of the present invention may further include, in addition to the sweeteners and the like, preservatives, emulsifiers, acidifiers, thickeners, and the like as needed.

These preservatives, emulsifiers, and the like may be added and used in a trace amount capable of achieving the purpose of addition and use. The term "trace amount" refers to, when numerically expressed, a range of about 0.0005 wt % to about 0.5 wt % with respect to the total weight of the food composition. Examples of suitable preservatives may include calcium sodium sorbate, sodium sorbate, potassium sorbate, calcium benzoate, sodium benzoate, potassium benzoate, ethylenediaminetetraacetic acid (EDTA), and the like. Examples of suitable emulsifiers may include acacia gum, carboxymethyl cellulose, xanthan gum, pectin, and the like. Examples of suitable acidifiers may include citric acid, malic acid, fumaric acid, adipic acid, phosphoric acid, gluconic acid, tartaric acid, ascorbic acid, acetic acid, and the like. These acidifiers may be added not only for the purpose of enhancing taste, but also for the purpose of inhibiting the growth of microorganisms such that the food composition has a proper acidity. Examples of suitable thickeners may include a suspending agent, a precipitating agent, a gel-forming agent, a bulking agent, and the like.

According to another embodiment of the present invention, there is provided a pharmaceutical composition for treating or preventing cancer, which includes the composition for inhibiting the growth of a cancer stem cell.

Figure 1A:
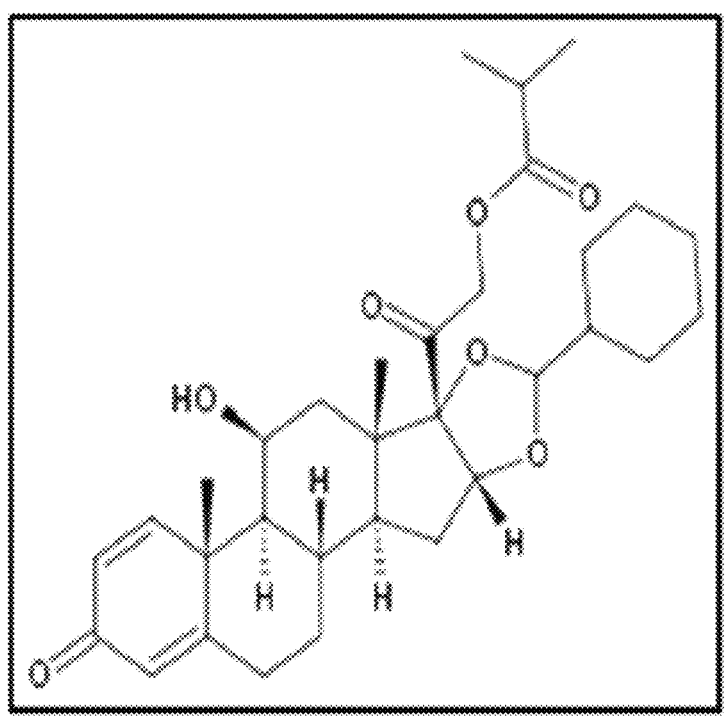
FIGS. 1A and 1B illustrate the chemical structure of ciclesonide and the survival rate of ciclesonide for MCF-7 cells and MDA-MB-231 cells, in which MCF-7 cells and MDA-MB-231 cells were treated with ciclesonide at increasing concentrations for 48 hours, and an anti-proliferative effect of ciclesonide was measured by MTS assay.
Figure 1B:
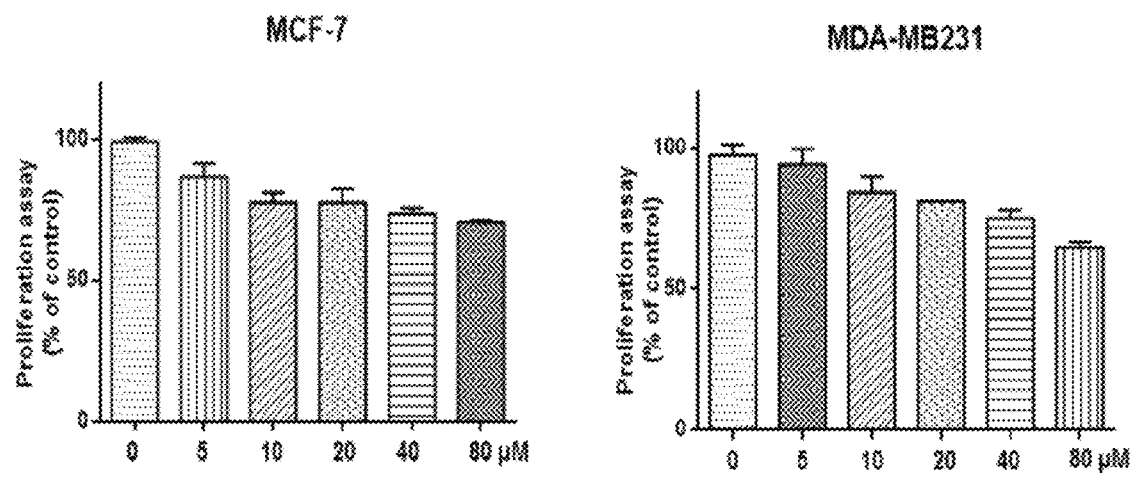

In one embodiment of the present invention, when an MCF-7 cell line and an MDA-MB-231 cell line were treated with ciclesonide, it was confirmed that the ciclesonide inhibited the growth of the breast cancer cell lines (see FIGS. 1A and 1B). It was also confirmed that, upon treatment with ciclesonide, apoptotic bodies were formed in the MDA-MB-231 cells (see FIG. 1E).

In another embodiment of the present invention, it was confirmed that, when A549 cells were treated with ciclesonide, the growth of lung cancer cell lines was inhibited (see FIG. 7A). It was also confirmed that, upon treatment with ciclesonide, apoptotic bodies were formed in the A549 cells (see FIG. 7B).

Accordingly, the composition of the present invention may be used as a pharmaceutical composition for treating or preventing breast cancer or lung cancer.

In addition, in one embodiment of the present invention, it was confirmed that the ciclesonide inhibitor reduced mother population expressing $CD44^{high}/CD24^{low}$ in breast cancer cells (see FIG. 4A) and reduced the proportion of ALDH-positive breast cancer cells (see FIG. 4B). It was also confirmed that the ciclesonide inhibitor reduced the proportion of ALDH-positive lung cancer cells (see FIG. 10). Accordingly, the composition may inhibit the growth of breast cancer cells expressing $CD44^{high}/CD24^{low}$, may inhibit the growth of aldehyde dehydrogenase (ALDH)-positive breast cancer cells, and may inhibit the growth of ALDH-positive lung cancer cells.

According to another embodiment of the present invention, there is provided a pharmaceutical composition for inhibiting cancer metastasis, which includes the composition for inhibiting the growth of a cancer stem cell.

The cancer is divided into primary cancer that is present at the site of development and metastatic cancer that spreads to other parts of the body from the development site. The term "cancer metastasis" as used herein refers to a condition in which malignant tumors have spread to other tissues distant from the organ with developed tumors. Cancer cells are formed by spreading through blood circulation or lymphatic circulation, and mostly develop into new tumors after being transferred to other organs via blood circulation. Unlike this, cancer cells are also formed by direct migration to neighboring tissues. In the present invention, cancer metastasis includes both spreading of cancer cells by invasion in which the cancer cells directly migrate and infiltrate into neighboring tissues and metastasis in which new tumors are formed in an organ not physically adjacent to the primary cancer by migration of cancer cells through blood flow. Meanwhile, in cancer metastasis, cell migration is essential. Therefore, it is obvious that inhibiting the migration of cancer cells is a primary method of preventing cancer metastasis.

In the present invention, the cancer may be, but is not limited to, breast cancer or lung cancer. The terms "cancer," "cancer stem cell," "inhibiting the growth of a cancer stem cell," and "pharmaceutical composition" as used herein are the same as defined above.

Figure 1C:
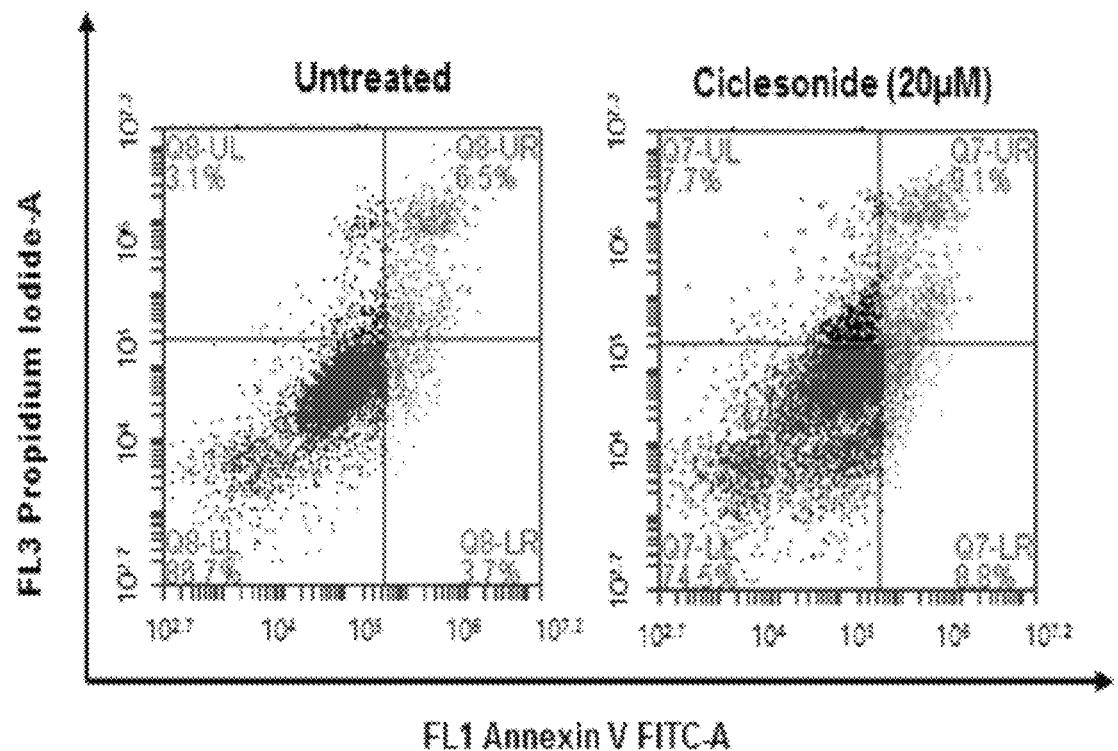
FIGS. 1C, 1D, and 1E illustrate an effect of ciclesonide on apoptosis of breast cancer cells wherein MDA-MB-231 cells were treated with ciclesonide for 24 hours, and apoptotic cells were analyzed by FACS using an annexin V-PI staining kit, caspase 3/7 activity in the MDA-MB-231 cells was analyzed using a Caspase-Glo 3/7 kit, apoptotic cells were analyzed by fluorescence staining, and nuclei of breast cancer cells were stained with Hoechst 33258 (at a magnification of 100×)
Figure 1D:
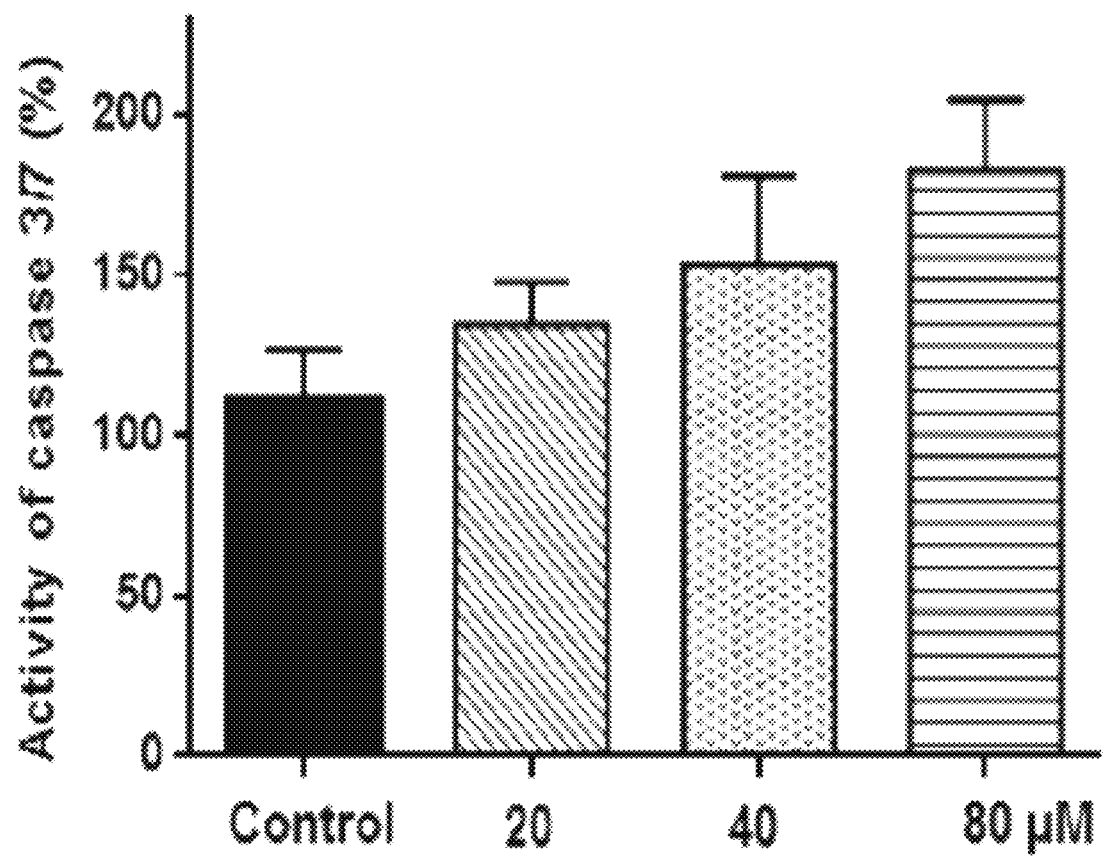
Figure 1E:
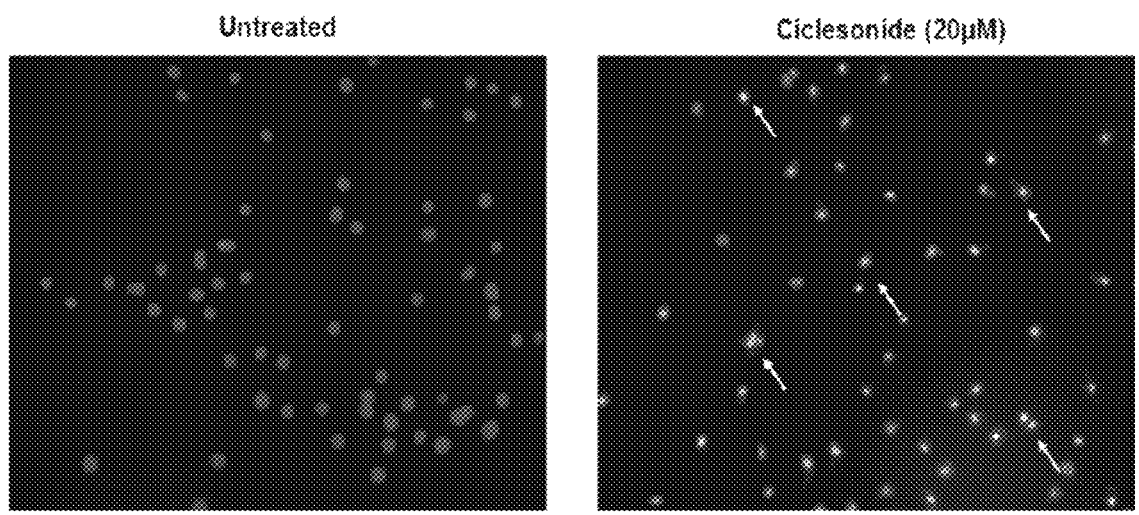
Figure 1F:
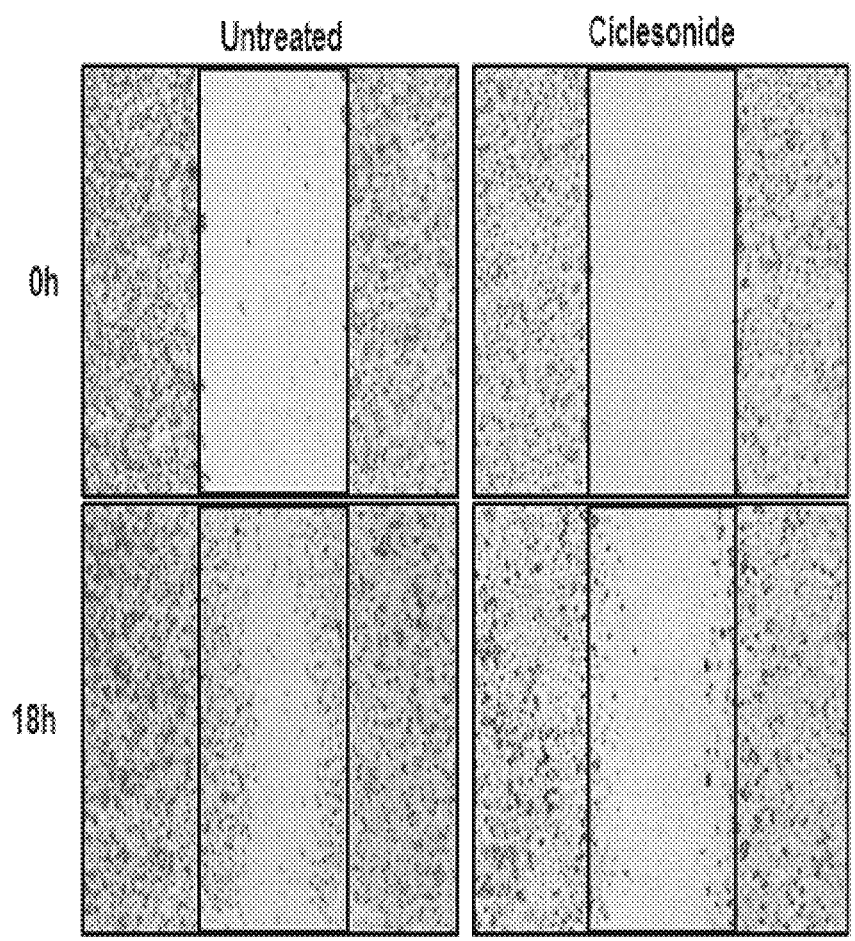
FIG. 1F illustrates an effect of ciclesonide on the migration potential of human breast cancer cells wherein wound healing of MDA-MB-231 cells were photographed at 0 hours and 18 hours depending on whether or not to be treated with ciclesonide.
Figure 1G:
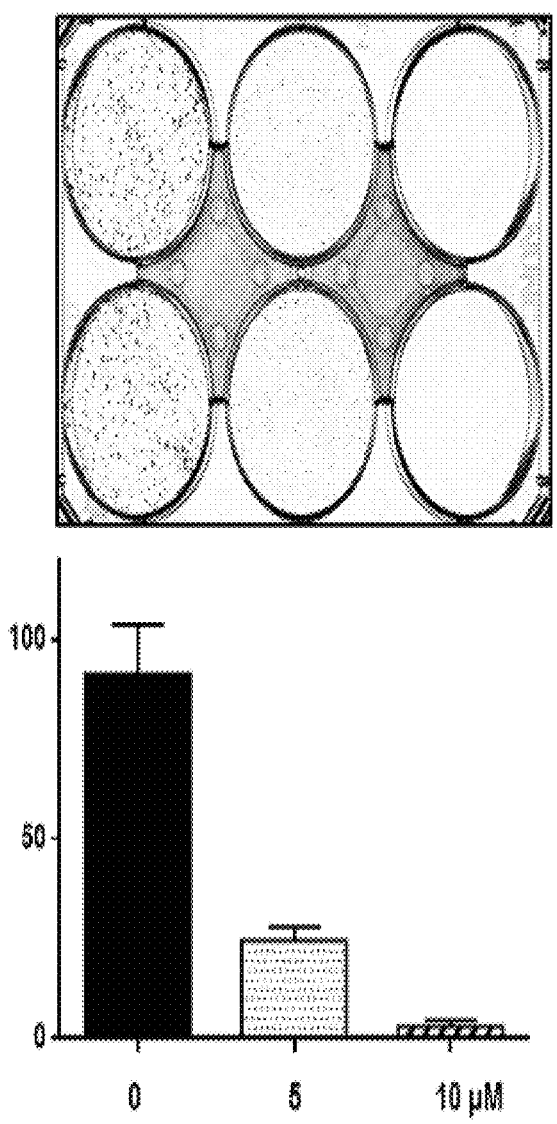
FIG. 1G illustrates an effect of ciclesonide on colony formation in human breast cancer cells, in which the dissociated 1,000 MDA-MB-231 cells were inoculated into a 6-well plate and treated with ciclesonide or DMSO for 7 days at indicated concentrations, representative images of colonies were recorded, and the displayed data was expressed as the mean±SD for the three independent experimental results. *$p<0.05$ vs. DMSO-treated control.

In one embodiment of the present invention, it was confirmed that ciclesonide inhibited the migration and colony formation of MDA-MB-231 cells in a concentration-dependent manner (see FIGS. 1F and 1G).

In addition, in another embodiment of the present invention, it was confirmed that ciclesonide inhibited the migration and colony formation of A549 cells (see FIGS. 7E and 7F).

Accordingly, the composition of the present invention may inhibit cancer metastasis by inhibiting the migration of cancer cells, and thus may be utilized as a pharmaceutical composition for inhibiting cancer metastasis.

According to another embodiment of the present invention, there is provided a food composition for alleviating or preventing cancer, which includes the composition for inhibiting the growth of a cancer stem cell.

The terms "cancer," "cancer stem cell," "inhibiting the growth of a cancer stem cell," and "food composition" as used herein are the same as defined above. In one embodiment of the present invention, it was confirmed that, when an MCF-7 cell line and an MDA-MB-231 cell line were treated with ciclesonide, the growth of the breast cancer cell lines was inhibited. In another embodiment, it was confirmed that, when an A549 cell line was treated with ciclesonide, the growth of the lung cancer cell lines was inhibited. Thus, the composition of the present invention may be used as a food composition for alleviating or preventing cancer. In the present invention, the cancer may be, but is not limited to, breast cancer or lung cancer.

According to another embodiment of the present invention, there is provided a food composition for alleviating or preventing cancer metastasis, which includes the composition for inhibiting the growth of a cancer stem cell.

The terms "cancer metastasis," "cancer stem cell," "inhibiting the growth of a cancer stem cell," and "food composition" as used herein are the same as defined above. In one embodiment of the present invention, it was confirmed that ciclesonide inhibited the migration and colony formation of MDA-MB-231 cells in a concentration-dependent manner. In another embodiment, it was confirmed that ciclesonide inhibited the migration and colony formation of A549 cells. Thus, the composition of the present invention may be used as a food composition for alleviating or preventing cancer metastasis. In the present invention, the cancer may be, but is not limited to, breast cancer or lung cancer.

According to another aspect of the present invention, there is provided a method of inhibiting the growth of a cancer stem cell, which includes administering ciclesonide represented by Formula 1 below or a pharmaceutically acceptable salt thereof to an individual.

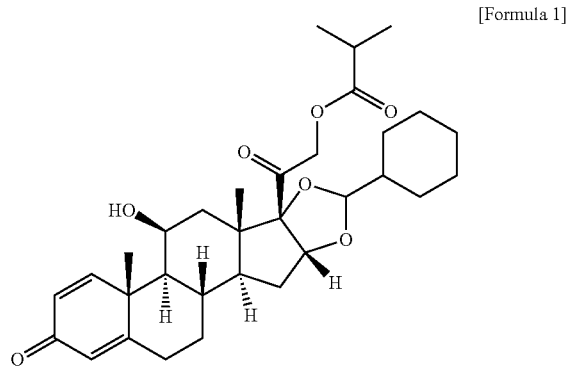

[Formula 1]

The terms "ciclesonide," "cancer," "cancer stem cell," and "inhibiting the growth of a cancer stem cell" as used herein are the same as defined above.

The term "individual" as used herein refers to all animals, including humans who have developed cancer metastasis or have developed cancer. The individual includes mammals including cows, pigs, sheep, chickens, dogs, humans, and the like, and includes, but is not limited to, individuals in which the growth of cancer stem cells is inhibited via administration of the composition of the present invention and cancer is treated thereby.

According to another embodiment of the present invention, there is provided a method of inhibiting cancer metastasis, which includes administering the ciclesonide of Formula 1 or a pharmaceutically acceptable salt thereof to an individual.

The terms "ciclesonide," "cancer," "individual," and "cancer metastasis" as used herein are the same as defined above.

According to another embodiment of the present invention, there is provided a method of treating or preventing cancer, which includes administering the ciclesonide of Formula 1 or a pharmaceutically acceptable salt thereof to an individual.

The terms "ciclesonide," "cancer," "individual," "treatment," and "prevention" as used herein are the same as defined above.

According to another embodiment of the present invention, there is provided a use of the ciclesonide of Formula 1 or a pharmaceutically acceptable salt thereof for preparing a drug for inhibiting the growth of a cancer stem cell.

The terms "ciclesonide," "cancer," "cancer stem cell," and "inhibiting the growth of a cancer stem cell" as used herein are the same as defined above.

According to another aspect of the present invention, there is provided a use of the ciclesonide of Formula 1 or a pharmaceutically acceptable salt thereof for preparing a drug for inhibiting cancer metastasis.

The terms "ciclesonide," "cancer," and "cancer metastasis" as used herein are the same as defined above.

According to another embodiment of the present invention, there is provided a use of the ciclesonide of Formula 1 or a pharmaceutically acceptable salt thereof for preparing a drug for preventing or treating cancer.

The terms "ciclesonide," "cancer," "treatment," and "prevention" as used herein are the same as defined above.

MODE FOR INVENTION

Hereinafter, the present invention will be described in further detail with reference to the following examples. These examples are provided for illustrative purposes only and are not intended to limit the scope of the present invention.

A: EXPERIMENTAL MATERIALS AND METHODS

Example 1

Experimental Materials 6-well culture plates including ultra-low attachment cluster plates were obtained from Corning (Tewksbury, Mass., USA). Ciclesonide was purchased from Sigma-Aldrich Co. (St. Louis, Mo., USA). Cell viability was measured using a CellTiter 96® aqueous one solution cell proliferation assay kit (Promega, Madison, Wis., USA). The ALDEFLUOR™ Kit was purchased from STEMCELL Technologies Inc (Vancouver, BC, Canada).

Example 2-1

Culture of Human Breast Cancer Cells and Formation of Mammospheres

Human breast cancer cells, MCF-7, were obtained from American Type Culture Collection (ATCC; Manassas, Va., USA). MCF-7 cells and MDA-MB-231 cells were cultured in Dulbecco's Modified Essential Medium (DMEM; Hyclone, Logan, Utah, USA) containing 10% fetal bovine serum (FBS; Hyclone), 100 U/ml of penicillin, and 100 μg/ml of streptomycin (Hyclone). The MCF-7 cells were maintained in a humidified incubator containing 5% $CO_2$ at 37° C. The cells were plated in 10 cm culture dishes at a density of $1\times10^6$ cells. To establish primary mammospheres, single cell-suspended MCF-7 cells were inoculated into ultra-low attachment 6-well plates containing 2 ml of complete MammoCult™ medium (StemCell Technologies, Vancouver, BC, Canada) at a density of 3.5 to $4\times10^4$ cells/well. The complete MammoCult™ medium was supplemented with 4 μg/ml of heparin, 0.48 μg/ml of hydrocortisone, 100 U/ml of penicillin, and 100 μg/ml of streptomycin. The cells were incubated in a 5% $CO_2$ incubator at 37° C. for 7 days.

Example 2-2

Culture of Human Lung Cancer Cells and Formation of Tumorspheres

Human lung cancer cells, A549, were cultured under the same culture conditions as those for the breast cancer cells of Example 2-1. To establish primary tumorspheres, single cell-suspended A549 cells were inoculated into ultra-low attachment 6-well plates containing 2 ml of Cancer Stem Premium medium (ProMab Biotechnologies Inc, Richmond, Calif., USA) at a density of $5\times10^4$ cells/well. The cells were incubated in a 5% $CO_2$ incubator at 37° C. for 10 days.

Example 3-1

Automatic Calculation of Breast Cancer Mammospheres

On day 10 of culture, cell culture plates were placed on a scanner (Epson Perfection V700 PHOTO, Epson Korea, Co, Seoul, Korea) to obtain 8-bit gray scale images of mammospheres. The images were acquired using a NICE software program downloaded from ftp://ftp.nist.gov/pub/physics/mlclarke/NICE at a low resolution of 300 dpi. For counting, a desired number of rows and columns (e.g., 2×3 for a 6-well plate) were selected to generate ROIs and after selecting the elliptical setting of the NICE program, the individual ROIs were defined by adjusting the movement and size of the provided ROI shapes. The background signals of the images were negated using a threshold algorithm, and the selected images were automatically counted. To analyze the formation of mammospheres, mammosphere formation efficiency (MFE, %) was determined by the following equation: MFE (%)=the number of mammospheres per well/a total number of plated cells per well×100.

Example 3-2

Automatic Calculation of Lung Cancer Tumorspheres

Lung cancer tumorspheres were counted in the same manner as in Example 3-1, and for the analysis of tumorsphere formation, tumorsphere formation efficiency (TFE, %) was determined by the following equation: TFE (%)=number of tumorspheres per well/total number of plated cells per well×100.

Example 4

Caspase-3/7 Analysis

Breast cancer cells and lung cancer cells were treated with ciclesonide at different concentrations for 24 hours. Caspase-3/7 activity was measured in accordance with the manufacturer's protocol for the Caspase-Glo 3/7 kit (Promega, Wisconsin, USA). 100 μl of a Caspase-Glo 3/7 reagent was added to a 96-well plate where cancer cells were cultured. The plate was covered with a plate sealer, followed by culture at room temperature for 1 hour, and measured using a plate-reading luminometer, GloMax® Explorer (Promega, Wisconsin, USA).

Example 5

CD44 and CD24 Expression Flow Cytometric Analysis

The expression of CD44 and CD24 in MCF-7 cells was measured by FACS analysis. After isolating and harvesting cells using 1× trypsin/EDTA, one million cells were suspended, labeled with an FITC-conjugated anti-human CD44 antibody and a PE-conjugated anti-human CD24 antibody (BD Pharmingen, San Diego, Calif., USA), and incubated at 4° C. for 30 minutes. The cells were then washed three times with 1× PBS and analyzed by flow cytometry (Accuri C6, BD, San Diego, Calif., USA).

Example 6

Analysis of Annexin V/PI Staining

Cancer cells were cultured in a 6-well plate for 24 hours along with 20 μM of ciclesonide for the case of breast cancer and 10 μM or 20 μM of ciclesonide or DMSO for the case of lung cancer. In accordance with the manufacturer's protocol, apoptotic cells were double-stained with PI and FITC-Annexin V. The sample was analyzed by flow cytometry (Accuri C6, BD, San Diego, Calif., USA).

Example 7

Apoptosis Analysis by Fluorescence Staining

MDA-MB-231 cells were treated with 20 μM ciclesonide or A549 cells were treated with 30 μM ciclesonide, for 24 hours and the cells were incubated in 10 mg/ml of a Hoechst 33258 solution at 37° C. for 30 minutes. Subsequently, the cells were observed using a fluorescence microscope.

Example 8

Clonogenic Assay

MDA-MB-231 cells or A549 cells were inoculated at low density in a 6-well plate, and, in a DMEM medium, the MDA-MB-231 cells were treated with different concentrations of ciclesonide, or the A549 cells were treated with 10 μM ciclesonide. After 24 hours, the medium was replaced with a new medium and cultured for 7 hours to allow the cells to grow. The grown colonies were counted.

Example 9

Scratch Migration Analysis

MDA-MB-231 cells or A549 cells were inoculated into a 6-well plate and grown to 90% confluency. A scratch was made on the cell layer using a sterile white micropipette tip. After washing with DMEM medium, the breast cancer cells or lung cancer cells were treated with ciclesonide or DMSO. At 18 hours, wounded areas were photographed using an optical microscope at a magnification of ×40.

Example 10-1

Breast Cancer Cell Proliferation Assay

The proliferation rates of MCF-7 cells and MDA-MB-231 cells were measured using a CellTiter 96® aqueous one solution cell proliferation kit. The MCF-7 cells or the MDA-MB-231 cells were cultured in a 96-well plate for 48 hours in the presence of ciclesonide at concentrations of 0 μM, 5 μM, 10 μM, 20 μM, 40 μM, and 80 μM. In accordance with the manufacturer's protocol, absorbance at 490 nm was determined using a 96-well plate reader (Dynex Revelation, Dynex Ltd., Billingshurst, UK). Respective data was determined by measuring three sets.

Example 10-2

Lung Cancer Cell Proliferation Assay

An experiment was performed in the same manner as in Example 10-1, except that A549 cells were used as lung cancer cells and treated with ciclesonide at concentrations of 0 μM, 10 μM, 20 μM, 40 μM, 80 μM, and 100 μM.

Example 11

Western Blotting

Proteins isolated from ciclesonide-treated MCF-7 or MDA-MB-231 mammospheres were separated on 10% SDS-PAGE and transferred to a polyvinylidene difluoride membrane (Millipore, Bedford, Mass., USA). The membrane was blocked in PBS-Tween 20 (0.1%, v/v) containing 5% skimmed milk at room temperature for 30 minutes. The blot was incubated at 4° C. overnight with a blocking solution containing primary antibodies. The primary antibodies used were as follows: Stat3, p65, Lamin B, and phospho-Stat3 (Cell Signaling, Beverly, Mass., USA). β-actin (Santa Cruz Biotechnology) was used as a loading control. After washing with PBS-Tween 20 (0.1%, v/v), the blot was incubated with horseradish peroxidase-conjugated secondary antibodies, and photosensitized with a chemiluminescence detection kit (Santa Cruz Biotechnology).

Example 12

ALDEFLUOR Analysis

An ALDEFLUOR analysis system provides a novel approach to the identification, evaluation, and isolation of CSCs based on the activity of aldehyde dehydrogenase (ALDH). BODIPY-aminoacetaldehyde as an active reagent was added to breast cancer cells or lung cancer cells, and converted into fluorescent BODIPY-aminoacetate by ALDH. Diethylaminobenzaldehyde (DEAB), which is an ALDH inhibitor, was used as a negative control. MCF-7 cells or A549 cells were treated with 10 μM or 20 μM ciclesonide for 24 hours, and the proportion of ALDH-positive cells was analyzed by ALDEFLUOR assay. ALDH-positive and negative cells were sorted by C6 Accuri flow cytometry (BD Bioscience).

Example 13-1

Chemotherapy of Breast Cancer Cell-Producing Immunodeficient NOD-SCID (BALB/cSlc (nu/nu)) Female Nude Mice A total of 12 NOD-SCID (BALB/cSlc (nu/nu)) female nude mice producing breast cancer cells were divided into two groups. 6 mice as a negative control did not receive chemotherapy. The volume of tumors of each control mouse was measured every three days and calculated by the following equation: (width×length$^2$)/2. The other six nude mice received neoadjuvant chemotherapy using a test drug by infusion at an optimum dose of 10 mg/kg/day.

Example 13-2

Chemotherapy of Lung Cancer Cell-Producing Immunodeficient NOD-SCID (BALB/cSIc (nu/nu)) Male Nude Mice A total of 12 NOD-SCID (BALB/cSIc (nu/nu)) male nude mice producing lung cancer cells were divided into two groups. 6 mice as a negative control did not receive chemotherapy. The volume of tumors of each control mouse was measured every three days and calculated by the following equation: (width×length$^2$)/2. The other six nude mice received neoadjuvant chemotherapy using a test drug by infusion at an optimum dose of 10 mg/kg/day.

Example 14

Real-Time PCR (RT-PCR)

The levels of transcripts were measured with a One Step SYBR PrimeScript RT-PCR kit (Takara, Tokyo, Japan) using SYBR green as a double-stranded DNA-specific dye in accordance with the manufacturer's protocol. One-step RT-PCR was performed on 1 µg of total RNA, 10 µl of 2× One Step SYBR RT-PCR Buffer IV, and 1 µl of PrimeScript 1 step Enzyme Mix II using PCR forward and reverse primers of each of CD44, NANOG, OCT4, C-myc, Sox2, Snail, and β-actin at a final volume of 20 µl per reaction.

The forward and reverse primers were as follows:

```
CD44 forward primer:
                           (SEQ ID NO: 1)
AGAAGGTGTGGGCAGAAGAA;

CD44 reverse primer:
                           (SEQ ID NO: 2)
AAATGCACCATTTCCTGAGA;

NANOG forward primer:
                           (SEQ ID NO: 3)
ATGCCTCACACGGAGACTGT;

NANOG reverse primer:
                           (SEQ ID NO: 4)
AAGTGGGTTGTTTGCCTTTG;

OCT4 forward primer:
                           (SEQ ID NO: 5)
AGCAAAACCCGGAGG;

OCT4 reverse primer:
                           (SEQ ID NO: 6)
CCACATCGGCCTGTGTATATC;

SOX2 forward primer:
                           (SEQ ID NO: 7)
TTGCTGCCTCTTTAAGACTAGGA;

SOX2 reverse primer:
                           (SEQ ID NO: 8)
CTGGGGCTCAAACTTCTCTC;

C-myc forward primer:
                           (SEQ ID NO: 9)
AATGAAAAGGCCCCCAAGGTAGTTATCC;

-continued
C-myc reverse primer:
                           (SEQ ID NO: 10)
GTCGTTTCCGCAACAAGTCCTCTTC;

β-actin forward primer:
                           (SEQ ID NO: 11)
TGTTACCAACTGGGACGACA;

β-actin reverse primer:
                           (SEQ ID NO: 12)
GGGGTGTTGAAGGTCTCAAA;

Snail forward primer:
                           (SEQ ID NO: 15)
ACCACTATGCCGCGCTCTT;
and Snail reverse primer:
                           (SEQ ID NO: 16)
GGTCGTAGGGCTGCTGGAA.
```

The relative expression level of mRNA of the target gene was calculated using a comparative CT method. At least three independent PCR procedures were performed in accordance with statistical analysis. PCR products were normalized with the p-actin gene as an internal control.

Example 15

Human Inflammatory Cytokine Assay

Inflammatory cytokines were measured using a BD cytometric bead array (BD) human inflammatory cytokines kit (BD, San Diego, Calif., USA) in accordance with the manufacturer's protocol.

Mixed capture beads were vortexed and 50 µl of beads were added to assay tubes. 50 µl of human inflammatory cytokine standard and the cultured tumorsphere solution were added to the assay tubes, and then mixed with a cytokine PE solution. After 3 hours, the mixed solution was washed and analyzed by flow cytometry (Accuri C6, BD, San Diego, Calif., USA).

Example 16

Electrophoretic Mobility Shift Assays (EMSA)

EMSA was performed using a Lightshift chemiluminescent EMSA kit (Thermoscientific, IL, USA) in accordance with the manufacturer's protocol. The biotin-upper and lower portions of the Stat3 probe (5-CTTCATTTCCCG-GAAATCCCTA-Biotin3, SEQ ID No: 13 and 5-TAGG-GATTTCCGGGAAATGAAG-Biotin3, SEQ ID NO: 14) were annealed and the double-stranded oligonucleotides were labeled with biotin. A nuclear extract was prepared from each of MCF-7, MDA-MB-231, and A549 cells as described in the reference (Choi H S, Hwang C K, Kim C S, Song K Y, Law P Y, Wei L N and Loh H H. Transcriptional regulation of mouse mu opioid receptor gene: Sp3 isoforms (M1, M2) function as repressors in neuronal cells to regulate the mu opioid receptor gene. Mol Pharmacol. 2005; 67(5): 1674-1683).

The biotin-labeled DNA probe was cultured with ciclesonide-treated nucleoproteins in a total of 20 µl of an EMSA buffer containing 1 µg/µL of poly [dI-dC] at room temperature for 20 minutes. The reaction mixture was electrophoresed on a 4% polyacrylamide unmodified gel in 0.5× TBE (45 mM Tris borate and 1 mM EDTA) at 4° C., and visualized using a chemiluminescent nucleic acid detection kit (Thermoscientific, IL, USA).

Example 17

Statistical Analysis

All data were expressed as mean±standard deviation (SD). The data was analyzed using a student's t-test. P values lower than 0.05 were considered statistically significant (GraphPad Prism 5 Software, San Diego, Calif., USA).

B: EXPERIMENTAL EXAMPLE

Analysis of Effects on Breast Cancer Stem Cells and Breast Cancer

Experimental Example 1

Effect of Ciclesonide on Inducing Apoptosis and Inhibiting Proliferation of Human Breast Cancer Cells To examine an anti-proliferative effect of ciclesonide illustrated in FIG. 1A on MCF-7 and MDA-MB-231, which are human breast cancer cell lines, each cell line was treated with ciclesonide at various concentrations, and then MTS analysis was performed. From the results, it was confirmed that, 48 hours after treatment with ciclesonide, growth of the breast cancer cell lines was inhibited in a concentration-dependent manner at a concentration of 10 µM or higher in the MCF-7 and MDA-MB-231 cell lines (see FIGS. 1A and 1B).

Next, it was confirmed that the number of apoptotic breast cancer cells (annexin V+) in the case of MDA-MB-231 cells was increased by treatment with 20 µM of ciclesonide (see FIG. 1C).

Next, a caspase 3/7 fluorescence assay was performed on the MDA-MB-231 cells, and from the results, it was confirmed that caspase 3/7 activity was induced at 40 µM and 80 µM of ciclesonide (see FIG. 1D). It was also confirmed that, upon treatment with ciclesonide, apoptotic bodies were formed in the MDA-MB-231 cells (see FIG. 1E). In addition, ciclesonide inhibited the migration and colony formation of MDA-MB-231 cells (see FIGS. 1F and 1G). These results indicate that ciclesonide effectively inhibits various cancer characteristics (proliferation, migration, apoptosis, and colony formation).

Experimental Example 2

Effect of Ciclesonide on Inhibiting Tumor Growth in Xenograft Model

Figure 2A:
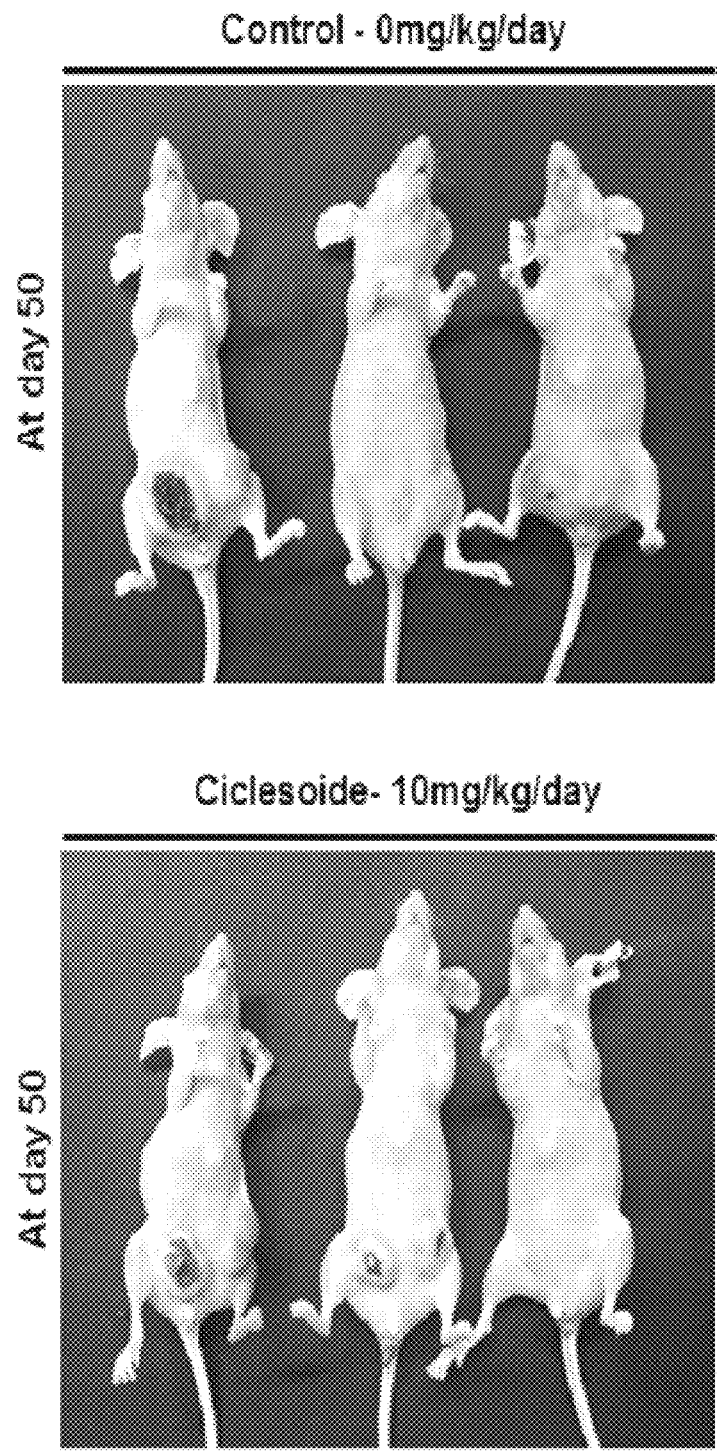
FIG. 2A illustrates an effect of ciclesonide on tumor growth in MCF-7 cell-producing immunodeficient nude mice wherein a dose of the drug used was 10 mg/kg.
Figure 2B:
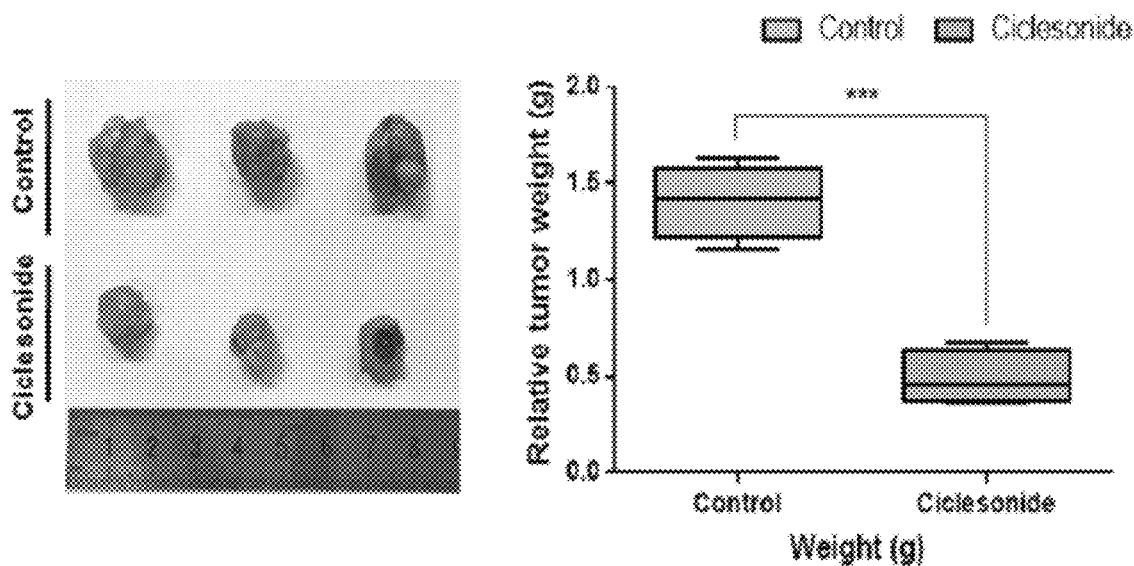
FIG. 2B illustrates an effect of ciclesonide on tumor weight wherein the tumor weight was measured after treatment.
Figure 2C:
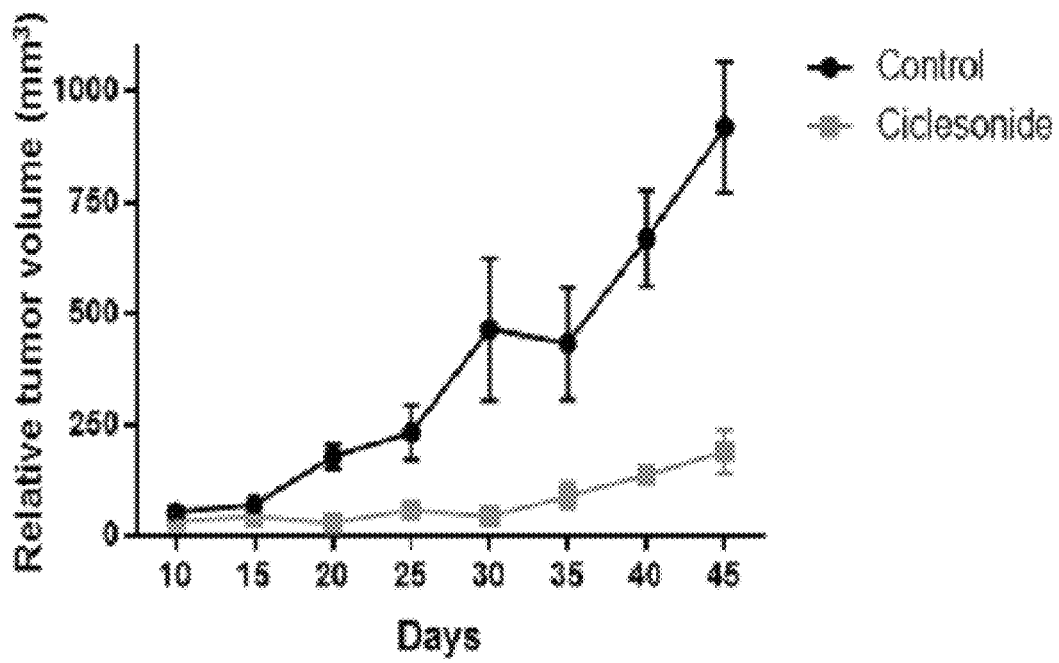
FIG. 2C illustrates tumor volume measured using calipers twice a week and calculated by (width×length$^2$)/2 wherein the tumor growth curve was monitored during the experimental period.

The effect of ciclesonide on inhibiting the proliferation of breast cancer cells was confirmed in FIG. 1. Next, it was examined whether ciclesonide inhibits tumor induction in a xenograft tumor model. Tumor volume was smaller in a ciclesonide-administered group than in a control not treated with ciclesonide (see FIGS. 2A and 2C). In addition, tumor weight was also smaller in the ciclesonide-treated group than in the control not treated with ciclesonide (see FIG. 2B). However, the body weights of mice in the ciclesonide-treated group were similar to those in the control (see FIG. 2A). These results indicate that ciclesonide effectively inhibits tumor generation in a xenograft model.

Experimental Example 3

Effect of Ciclesonide on Inhibiting Breast Cancer Stem Cells

To evaluate whether ciclesonide is capable of inhibiting mammosphere formation, primary mammospheres derived from MCF-7 or MDA-MB-231 cells were treated with different concentrations of ciclesonide. As illustrated in FIG. 3, ciclesonide inhibited the formation of the breast cancer cell line-derived primary mammospheres. The number of the mammospheres was reduced by 90%, and the size of the mammospheres was also reduced (see FIGS. 3A and 3B).

Next, comparative experiments were carried out using prednisone and dexamethasone, which are currently and widely used glucocorticoids, and from the experimental results, it was confirmed that, while the growth of breast cancer stem cells was significantly inhibited at 10 µM ciclesonide, prednisone and dexamethasone, which belong to the same glucocorticoids, were unable to inhibit the growth of breast cancer stem cells at a high concentration, i.e., 80 µM (see FIG. 3C).

Thus, it was seen that, unlike existing steroids, ciclesonide effectively inhibited breast cancer stem cells.

Experimental Example 4

Effect of Ciclesonide on Reducing Proportions of CD44high/CD24low-Expressing Subpopulation and ALDH-Positive Breast Cancer Cells MCF-7 cells were treated with ciclesonide for 24 hours, and an effect of the ciclesonide inhibitor on a subpopulation expressing CD44high/CD24low in breast cancer cells was examined. As a result, the ciclesonide inhibitor reduced the subpopulation expressing CD44high/CD24low in breast cancer cells (see FIG. 4A). MCF-7 cells were treated with ciclesonide for 24 hours, and ALDEFLUOR analysis was performed to examine an effect of the ciclesonide inhibitor on the proportion of ALDH-positive breast cancer cells. From the results, it was confirmed that ciclesonide reduced the proportion of the ALDH-positive breast cancer cells (see FIG. 4B).

Experimental Example 5

Effect of Ciclesonide on Inhibiting STAT3 Signaling Pathway in Mammospheres To investigate the cellular function of ciclesonide, the phosphorylation state of STAT3 was examined in MCF-7 cells-derived mammospheres upon treatment with ciclesonide. As a result, ciclesonide reduced the phosphorylation of nuclear STAT3 protein compared to a control (see FIG. 5A).

In addition, a biotin-labeled SIE binding probe that has high binding affinity with STAT3 was used to analyze binding between a ciclesonide-treated nuclear extract and Stat3 DNA. As illustrated in FIG. 5B, ciclesonide inhibited binding between the biotin-labeled SIE probe and Stat3 (see FIG. 5B, lane 3). The specificity of the pStat3/biotin-labeled SIE probe was determined by an unlabeled excess self-competitor (see FIG. 5B, lane 4) and a mutated SIE competitor (see FIG. 5B, lane 5). From these data, it can be seen that the Stat3 signaling pathway is important in regulating the growth and self-renewal of mammospheres.

Experimental Example 6

Effect of Ciclesonide on Proliferation of MDA-MB-231 Cell-Derived Mammospheres and Production of IL-6 and IL-8

Secreted IL-6 and IL-8 have been known to play an important role in mammosphere formation (Sansone P, Storci G, Tavolari S, Guarnieri T, Giovannini C, Taffurelli M, Ceccarelli C, Santini D, Paterini P, Marcu K B, Chieco P and Bonafe M. IL-6 triggers malignant features in mammospheres from human ductal breast carcinoma and normal mammary gland. J Clin Invest. 2007; 117(12):3988-4002). Thus, to confirm the production of secreted IL-6 and IL-8, a flow cytometer was used to perform inflammatory cytokine profile analysis.

As a result, as shown in inflammatory cytokine profiling data, the production levels of IL-6 and IL-8 secreted were reduced by ciclesonide treatment. As an internal control, an MDA-MB-231 mammosphere culture solution not treated with ciclesonide was used (see FIG. 5C).

Experimental Example 7

Effect of Ciclesonide on Inhibiting Expression of Self-Renewing Genes of CSCs and Proliferation of Mammospheres To confirm whether ciclesonide inhibits the expression of self-renewing genes, the expression of self-renewing genes was examined by real-time PCR (RT-PCR). As a result, ciclesonide reduced the expression of self-renewing genes such as Nanog, Sox2, Oct4, C-myc, and CD44 in breast cancer cells (see FIG. 6A).

Next, to confirm whether ciclesonide inhibits the proliferation of mammospheres, the mammospheres were treated with ciclesonide and counted. As a result, ciclesonide induced apoptosis of the mammospheres, and the number of cells observed was smaller in the ciclesonide-treated mammospheres. From these results, it was confirmed that ciclesonide significantly reduced the proliferation of mammospheres (see FIG. 6B).

C: EXPERIMENTAL EXAMPLE

Analysis of Effects on Lung Cancer Stem Cells and Lung Cancer

Experimental Example 8

Effect of Ciclesonide on Inducing Apoptosis and Inhibiting Proliferation of Human Lung Cancer Cells To examine an anti-proliferative effect of ciclesonide on A549, which is a human lung cancer cell line, A549 cells were treated with ciclesonide illustrated in FIG. 7A at various concentrations, and then MTS analysis was performed. From the results, it was confirmed that, 48 hours after treatment with ciclesonide, the growth of lung cancer cell lines was inhibited in a concentration-dependent manner at 40 μM or more ciclesonide in the A549 cell line (see FIG. 7A).

It was also confirmed that, upon treatment with ciclesonide, apoptotic bodies were formed in the A549 cells (see FIG. 7B).

Next, it was confirmed that the number of apoptotic lung cancer cells (annexin V+) in the case of A549 cells was increased by treatment with 10 μM and 20 μM ciclesonide (see FIG. 7C). In addition, caspase 3/7 fluorescence analysis was performed on the A549 cells and, from the results, it was confirmed that ciclesonide induced caspase 3/7 activity at a concentration of 80 μM (see FIG. 7D). In addition, ciclesonide inhibited the migration and colony formation of A549 cells (see FIGS. 7E and 7F). These results indicate that ciclesonide effectively inhibits various cancer characteristics (proliferation, migration, apoptosis, and colony formation).

Experimental Example 9

Effect of Ciclesonide on Inhibiting Tumor Growth in Xenograft Model

The effect of ciclesonide on inhibiting the proliferation of lung cancer cells was confirmed in FIG. 7. Next, tumors were formed using lung cancer cells to produce a xenograft tumor model, the xenograft tumor model was treated with ciclesonide, and the size of tumors was measured every week to verify the effect of ciclesonide. As a result, tumor volume was smaller in a ciclesonide-administered group than in a control not treated with ciclesonide (see FIGS. 8A and 8C). In addition, tumor weight was also smaller in the ciclesonide-treated group than in the control not treated with ciclesonide (see FIG. 8B). However, the body weights of mice in the ciclesonide-treated group were similar to those in the control. These results indicate that ciclesonide effectively inhibits tumor generation in a xenograft model. That is, it means that ciclesonide has an excellent effect on reducing tumor size and weight and is effective for the treatment of lung cancer.

Experimental Example 10

Effect of Ciclesonide on Inhibiting Lung Cancer Stem Cells

To evaluate whether ciclesonide is capable of inhibiting the formation of tumorspheres, A549 cell-derived primary tumorspheres were treated with ciclesonide at different concentrations. As illustrated in FIG. 9A, ciclesonide inhibited the formation of primary tumorspheres derived from A549 cells, which are a lung cancer cell line. The number of the tumorspheres was reduced by 90%, and the size of the tumorspheres was also significantly reduced (see FIG. 9A).

In addition, as a result of treatment with isobutyryl ciclesonide, which is an activated form of ciclesonide, it was confirmed that isobutyryl ciclesonide exhibited a lung cancer stem cell inhibitory activity at concentrations of 5 μM and 10 μM.

In contrast, prednisone and dexamethasone, which are glucocorticoids, did not exhibit a lung cancer stem cell inhibitory activity even at a concentration of 80 μM (see FIG. 9C).

Thus, it was confirmed that isobutyryl ciclesonide, which is an activated form of ciclesonide, more effectively inhibited lung cancer-derived cancer stem cells than existing steroids, and all glucocorticoids did not inhibit the growth of lung cancer stem cells.

Experimental Example 11

Effect of Ciclesonide on Reducing Proportion of ALDH-Positive Lung Cancer Cells

Next, lung cancer cells were treated with DEAB, which is an ALDH inhibitor and ciclesonide to analyze ALDH, which is a lung cancer stem cell marker.

A549 cells were treated with ciclesonide for 24 hours, and ALDEFLUOR analysis was performed to examine an effect of the ciclesonide inhibitor on the proportion of ALDH-positive lung cancer cells. From the results, it was confirmed that ciclesonide reduced the proportion of the ALDH-positive lung cancer cells (see FIG. 10).

Experimental Example 12

Effect of Ciclesonide on Inhibiting Expression of CSC Markers and Proliferation of Tumorspheres To confirm whether ciclesonide inhibits the expression of self-renewing genes, which are CSC markers, the expression of self-renewing genes was examined by RT-PCR. From the results, it was confirmed that, upon treatment with ciclesonide, the expression of the Nanog, Sox2, C-myc, and Snail genes was reduced compared to a group not treated with ciclesonide (see FIG. 11A).

Next, to confirm whether ciclesonide inhibits the proliferation of tumorspheres, the tumorspheres were treated with ciclesonide and counted. As a result of analyzing the number of survived cancer cells in the tumorspheres on day 1, day 3, and day 3 after ciclesonide treatment, it was confirmed that, while the growth of tumorspheres was inhibited in the ciclesonide-treated group, the growth of tumorspheres progressed in a non-treated group (see FIG. 11B). Thus, it can be seen that ciclesonide significantly reduces the proliferation of tumorspheres (see FIG. 11B).

Experimental Example 13

Effect of Ciclesonide on Inhibiting Secretion of IL-8 in Tumorspheres

Secreted IL-8 has been known to play an important role in the formation of tumorspheres (Ginestier C, Liu S, Diebel M E, Korkaya H, Luo M, Brown M, Wicinski J, Cabaud O, Charafe-Jauffret E, Birnbaum D, Guan J L, Dontu G and Wicha M S. CXCR1 blockade selectively targets human breast cancer stem cells in vitro and in xenografts. J Clin Invest. 2010; 120(2):485-497).

Thus, to confirm the production of secreted IL-8, a flow cytometer was used to perform inflammatory cytokine profile analysis. The inflammatory cytokines were measured using a BD cytometric bead array (CBA) human inflammatory cytokines kit. CBA analysis was performed using antibodies IL-6, IL-8, IL-10, IL-12, IL-1β, and TNF. As a result, as shown in inflammatory cytokine profiling data of FIG. 12, the production level of IL-8, which is an inflammatory cytokine, was reduced by treatment with ciclesonide. The production of IL-8 was represented as a graph in the lower side of FIG. 12. Thus, it can be seen that ciclesonide inhibits lung cancer stem cells by inhibiting the secretion of IL-8, which is essential for the maintenance of cancer stem cells.

From the experimental examples, it was confirmed that the ciclesonide of the present invention not only inhibited the proliferation of breast cancer and lung cancer, but also inhibited the growth of breast cancer stem cells and lung cancer stem cells, and therefore, the ciclesonide of the present invention can be used to inhibit the growth of breast cancer cells, lung cancer cells, breast cancer stem cells, and lung cancer stem cells.

From the foregoing description, it will be understood by those skilled in the art to which the present invention pertains that the disclosure may be embodied in other specific forms without departing from the spirit or essential characteristics thereof. In this regard, it should be understood that the above-described embodiments are for illustrative purposes only and not for the purpose of limitation in any way. The scope of the present invention should be defined by the following claims, not by the detailed description such that all changes or modified forms made from the meaning and scope of the appended claims and equivalents thereto are within the scope of the present invention.

The invention claimed is:

1. A method of inhibiting growth of a cancer stem cell, comprising administering a composition comprising a compound represented by Formula 1 below or a pharmaceutically acceptable salt thereof as an active ingredient:

[Formula 1]

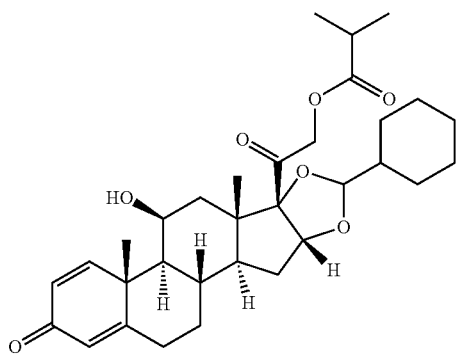

wherein the cancer stem cell is a breast cancer stem cell or a lung cancer stem cell, and wherein the composition inhibits formation of breast cancer-derived mammospheres (i), inhibits proliferation of breast cancer-derived mammospheres (ii), inhibits formation of lung cancer-derived tumorspheres (iii), or inhibits proliferation of lung cancer-derived tumorspheres (iv).

2. The method according to claim 1, wherein the compound is ciclesonide.

3. The method according to claim 1, wherein the breast cancer stem cell expresses at least one self-renewal gene selected from Nanog, C-myc, Oct4, Sox2, and CD44, or the lung cancer stem cell expresses at least one self-renewal gene selected from Nanog, Sox2, C-myc, and Snail.

4. A method of treating cancer, comprising administering an effective amount of a pharmaceutical composition comprising a compound represented by Formula 1 below or a pharmaceutically acceptable salt thereof as an active ingredient:

[Formula 1]

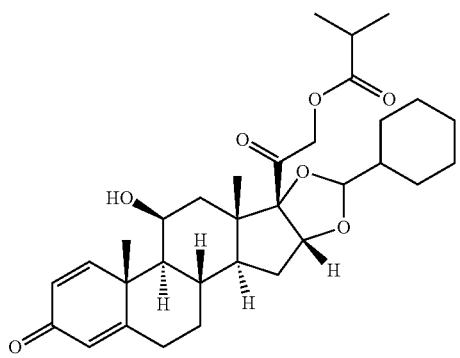

wherein the cancer is breast cancer or lung cancer, and wherein the pharmaceutical composition inhibits growth of breast cancer cells expressing CD44high/CD24low, growth of aldehyde dehydrogenase (ALDH)-positive breast cancer cells, or inhibits growth of ALDH-positive lung cancer cells.

5. A method of inhibiting metastasis of cancer, comprising administering an effective amount of a pharmaceutical composition comprising a compound represented by Formula 1 below or a pharmaceutically acceptable salt thereof as an active ingredient:

[Formula 1]

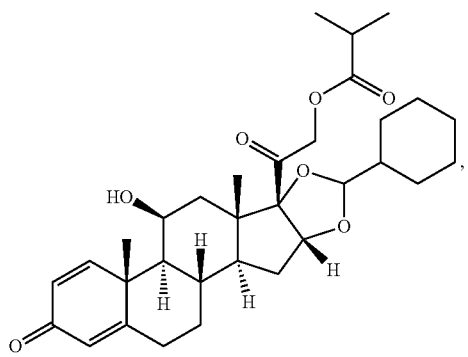

wherein the cancer is breast cancer or lung cancer, and wherein the pharmaceutical composition inhibits growth of breast cancer cells expressing CD44high/CD24low, growth of aldehyde dehydrogenase (ALDH)-positive breast cancer cells, or inhibits growth of ALDH-positive lung cancer cells.

6. A method of alleviating cancer, comprising administering an effective amount of a food composition comprising a compound represented by Formula 1 below as an active ingredient:

[Formula 1]

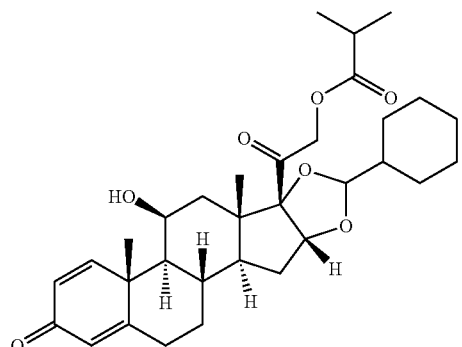

wherein the cancer is breast cancer or lung cancer, and wherein the food composition inhibits growth of breast cancer cells expressing CD44high/CD24low, growth of aldehyde dehydrogenase (ALDH)-positive breast cancer cells, or inhibits growth of ALDH-positive lung cancer cells.

7. A method of alleviating cancer metastasis, comprising administering an effective amount of a food composition comprising a compound represented by Formula 1 below as an active ingredient:

[Formula 1]

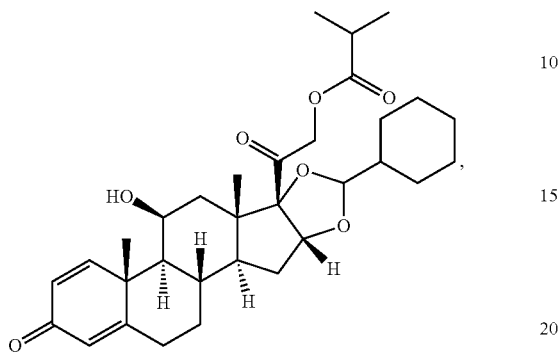

wherein the cancer is breast cancer or lung cancer, and wherein the food composition inhibits growth of breast cancer cells expressing CD44high/CD24low, growth of aldehyde dehydrogenase (ALDH)-positive breast cancer cells, or inhibits growth of ALDH-positive lung cancer cells.

* * * * *